(12) United States Patent
Mannheimer

(10) Patent No.: US 8,391,941 B2
(45) Date of Patent: Mar. 5, 2013

(54) SYSTEM AND METHOD FOR MEMORY SWITCHING FOR MULTIPLE CONFIGURATION MEDICAL SENSOR

(75) Inventor: Paul D. Mannheimer, Danville, CA (US)

(73) Assignee: Covidien LP, Mansfield, MA (US)

( * ) Notice: Subject to any disclaimer, the term of this patent is extended or adjusted under 35 U.S.C. 154(b) by 885 days.

(21) Appl. No.: 12/504,741

(22) Filed: Jul. 17, 2009

(65) Prior Publication Data
US 2011/0015507 A1 Jan. 20, 2011

(51) Int. Cl.
*A61B 5/1455* (2006.01)
(52) U.S. Cl. .......................... 600/323; 600/310; 600/344
(58) Field of Classification Search .................. 600/310, 600/322, 323, 344
See application file for complete search history.

(56) References Cited

U.S. PATENT DOCUMENTS

| | | | |
|---|---|---|---|
| 3,721,813 A | 3/1973 | Condon et al. |
| 4,586,513 A | 5/1986 | Hamaguri |
| 4,603,700 A | 8/1986 | Nichols et al. |
| 4,621,643 A | 11/1986 | New, Jr. et al. |
| 4,653,498 A | 3/1987 | New, Jr. et al. |
| 4,685,464 A | 8/1987 | Goldberger et al. |
| 4,694,833 A | 9/1987 | Hamaguri |
| 4,697,593 A | 10/1987 | Evans et al. |
| 4,700,708 A | 10/1987 | New, Jr. et al. |
| 4,714,080 A | 12/1987 | Edgar, Jr. et al. |
| 4,714,341 A | 12/1987 | Hamaguri et al. |
| 4,759,369 A | 7/1988 | Taylor |
| 4,770,179 A | 9/1988 | New, Jr. et al. |
| 4,773,422 A | 9/1988 | Isaacson et al. |
| 4,776,339 A | 10/1988 | Schreiber |
| 4,781,195 A | 11/1988 | Martin |
| 4,796,636 A | 1/1989 | Branstetter et al. |
| 4,800,495 A | 1/1989 | Smith |
| 4,800,885 A | 1/1989 | Johnson |
| 4,802,486 A | 2/1989 | Goodman et al. |
| 4,805,623 A | 2/1989 | Jöbsis |
| 4,807,630 A | 2/1989 | Malinouskas |
| 4,807,631 A | 2/1989 | Hersh et al. |
| 4,819,646 A | 4/1989 | Cheung et al. |
| 4,819,752 A | 4/1989 | Zelin |
| 4,824,242 A | 4/1989 | Frick et al. |

(Continued)

FOREIGN PATENT DOCUMENTS

| EP | 0630203 | 12/1994 |
|---|---|---|
| JP | 27020836 | 2/2007 |

(Continued)

OTHER PUBLICATIONS

International Search Report PCT/US2010/039307, 5 pages, mailed Jan. 24, 2011.

*Primary Examiner* — Eric Winakur
(74) *Attorney, Agent, or Firm* — Fletcher Yoder

(57) ABSTRACT

A system is provided that includes a monitor, a multiple configuration sensor having a first configuration and a second configuration, and a sensor connector. The sensor connector includes a first memory device and a second memory device, such that the first memory device is accessible by the monitor in the first sensor configuration and the second memory device is accessible by the monitor in the second sensor configuration. Another system is provided that includes a sensor adaptor having a processing circuit that reads a memory of a multiple configuration sensor and provides a first set of calibration data of a first sensor configuration and a second set of calibration data for a second sensor configuration.

20 Claims, 9 Drawing Sheets

U.S. PATENT DOCUMENTS

| | | |
|---|---|---|
| 4,825,872 A | 5/1989 | Tan et al. |
| 4,825,879 A | 5/1989 | Tan et al. |
| 4,830,014 A | 5/1989 | Goodman et al. |
| 4,832,484 A | 5/1989 | Aoyagi et al. |
| 4,846,183 A | 7/1989 | Martin |
| 4,848,901 A | 7/1989 | Hood, Jr. |
| 4,854,699 A | 8/1989 | Edgar, Jr. |
| 4,859,056 A | 8/1989 | Prosser et al. |
| 4,859,057 A | 8/1989 | Taylor et al. |
| 4,863,265 A | 9/1989 | Flower et al. |
| 4,865,038 A | 9/1989 | Rich et al. |
| 4,867,557 A | 9/1989 | Takatani et al. |
| 4,869,253 A | 9/1989 | Craig, Jr. et al. |
| 4,869,254 A | 9/1989 | Stone et al. |
| 4,880,304 A | 11/1989 | Jaeb et al. |
| 4,883,055 A | 11/1989 | Merrick |
| 4,883,353 A | 11/1989 | Hausman et al. |
| 4,890,619 A | 1/1990 | Hatschek |
| 4,892,101 A | 1/1990 | Cheung et al. |
| 4,901,238 A | 2/1990 | Suzuki et al. |
| 4,908,762 A | 3/1990 | Suzuki et al. |
| 4,911,167 A | 3/1990 | Corenman et al. |
| 4,913,150 A | 4/1990 | Cheung et al. |
| 4,926,867 A | 5/1990 | Kanda et al. |
| 4,927,264 A | 5/1990 | Shiga et al. |
| 4,928,692 A | 5/1990 | Goodman et al. |
| 4,934,372 A | 6/1990 | Corenman et al. |
| 4,938,218 A | 7/1990 | Goodman et al. |
| 4,942,877 A | 7/1990 | Sakai et al. |
| 4,948,248 A | 8/1990 | Lehman |
| 4,955,379 A | 9/1990 | Hall |
| 4,960,126 A | 10/1990 | Conlon et al. |
| 4,964,408 A | 10/1990 | Hink et al. |
| 4,971,062 A | 11/1990 | Hasebe et al. |
| 4,974,591 A | 12/1990 | Awazu et al. |
| 5,007,423 A | 4/1991 | Branstetter et al. |
| 5,025,791 A | 6/1991 | Niwa |
| RE33,643 E | 7/1991 | Isaacson et al. |
| 5,028,787 A | 7/1991 | Rosenthal et al. |
| 5,035,243 A | 7/1991 | Muz |
| 5,040,539 A | 8/1991 | Schmitt et al. |
| 5,054,488 A | 10/1991 | Muz |
| 5,055,671 A | 10/1991 | Jones |
| 5,058,588 A | 10/1991 | Kaestle |
| 5,065,749 A | 11/1991 | Hasebe et al. |
| 5,066,859 A | 11/1991 | Karkar et al. |
| 5,069,213 A | 12/1991 | Polczynski |
| 5,078,136 A | 1/1992 | Stone et al. |
| 5,084,327 A | 1/1992 | Stengel |
| 5,088,493 A | 2/1992 | Giannini et al. |
| 5,090,410 A | 2/1992 | Saper et al. |
| 5,094,239 A | 3/1992 | Jaeb et al. |
| 5,094,240 A | 3/1992 | Muz |
| 5,099,841 A | 3/1992 | Heinonen et al. |
| 5,099,842 A | 3/1992 | Mannheimer et al. |
| H0001039 H | 4/1992 | Tripp et al. |
| 5,104,623 A | 4/1992 | Miller |
| 5,109,849 A | 5/1992 | Goodman et al. |
| 5,111,817 A | 5/1992 | Clark et al. |
| 5,113,861 A | 5/1992 | Rother |
| 5,125,403 A | 6/1992 | Culp |
| 5,127,406 A | 7/1992 | Yamaguchi |
| 5,131,391 A | 7/1992 | Sakai et al. |
| 5,140,989 A | 8/1992 | Lewis et al. |
| 5,152,296 A | 10/1992 | Simons |
| 5,154,175 A | 10/1992 | Gunther |
| 5,158,082 A | 10/1992 | Jones |
| 5,170,786 A | 12/1992 | Thomas et al. |
| 5,188,108 A | 2/1993 | Secker et al. |
| 5,190,038 A | 3/1993 | Polson et al. |
| 5,193,542 A | 3/1993 | Missanelli et al. |
| 5,193,543 A | 3/1993 | Yelderman |
| 5,203,329 A | 4/1993 | Takatani et al. |
| 5,209,230 A | 5/1993 | Swedlow et al. |
| 5,213,099 A | 5/1993 | Tripp et al. |
| 5,216,598 A | 6/1993 | Branstetter et al. |
| 5,217,012 A | 6/1993 | Young et al. |
| 5,217,013 A | 6/1993 | Lewis et al. |
| 5,218,962 A | 6/1993 | Mannheimer et al. |
| 5,224,478 A | 7/1993 | Sakai et al. |
| 5,226,417 A | 7/1993 | Swedlow et al. |
| 5,228,440 A | 7/1993 | Chung et al. |
| 5,237,994 A | 8/1993 | Goldberger |
| 5,239,185 A | 8/1993 | Ito et al. |
| 5,246,002 A | 9/1993 | Prosser |
| 5,246,003 A | 9/1993 | DeLonzor |
| 5,247,931 A | 9/1993 | Norwood |
| 5,247,932 A | 9/1993 | Chung et al. |
| 5,249,576 A | 10/1993 | Goldberger et al. |
| 5,253,645 A | 10/1993 | Friedman et al. |
| 5,253,646 A | 10/1993 | Delpy et al. |
| 5,259,381 A | 11/1993 | Cheung et al. |
| 5,259,761 A | 11/1993 | Schnettler et al. |
| 5,263,244 A | 11/1993 | Centa et al. |
| 5,267,562 A | 12/1993 | Ukawa et al. |
| 5,267,563 A | 12/1993 | Swedlow et al. |
| 5,273,036 A | 12/1993 | Kronberg et al. |
| 5,275,159 A | 1/1994 | Griebel |
| 5,279,295 A | 1/1994 | Martens et al. |
| 5,285,783 A | 2/1994 | Secker |
| 5,285,784 A | 2/1994 | Seeker |
| 5,287,853 A | 2/1994 | Vester et al. |
| 5,291,884 A | 3/1994 | Heinemann et al. |
| 5,297,548 A | 3/1994 | Pologe |
| 5,299,120 A | 3/1994 | Kaestle |
| 5,299,570 A | 4/1994 | Hatschek |
| 5,309,908 A | 5/1994 | Friedman et al. |
| 5,311,865 A | 5/1994 | Mayeux |
| 5,313,940 A | 5/1994 | Fuse et al. |
| 5,323,776 A | 6/1994 | Blakely et al. |
| 5,329,922 A | 7/1994 | Atlee, III |
| 5,337,744 A | 8/1994 | Branigan |
| 5,339,810 A | 8/1994 | Ivers et al. |
| 5,343,818 A | 9/1994 | McCarthy et al. |
| 5,343,869 A | 9/1994 | Pross et al. |
| 5,348,003 A | 9/1994 | Caro |
| 5,348,004 A | 9/1994 | Hollub et al. |
| 5,349,519 A | 9/1994 | Kaestle |
| 5,349,952 A | 9/1994 | McCarthy et al. |
| 5,349,953 A | 9/1994 | McCarthy et al. |
| 5,351,685 A | 10/1994 | Potratz |
| 5,353,799 A | 10/1994 | Chance |
| 5,355,880 A | 10/1994 | Thomas et al. |
| 5,355,882 A | 10/1994 | Ukawa et al. |
| 5,361,758 A | 11/1994 | Hall et al. |
| 5,365,066 A | 11/1994 | Krueger, Jr. et al. |
| 5,368,025 A | 11/1994 | Young et al. |
| 5,368,026 A | 11/1994 | Swedlow et al. |
| 5,368,224 A | 11/1994 | Richardson et al. |
| 5,372,136 A | 12/1994 | Steuer et al. |
| 5,377,675 A | 1/1995 | Ruskewicz et al. |
| 5,385,143 A | 1/1995 | Aoyagi |
| 5,387,122 A | 2/1995 | Goldberger et al. |
| 5,390,670 A | 2/1995 | Centa et al. |
| 5,392,777 A | 2/1995 | Swedlow et al. |
| 5,398,680 A | 3/1995 | Polson et al. |
| 5,402,777 A | 4/1995 | Warring et al. |
| 5,411,023 A | 5/1995 | Morris, Sr. et al. |
| 5,411,024 A | 5/1995 | Thomas et al. |
| 5,413,099 A | 5/1995 | Schmidt et al. |
| 5,413,100 A | 5/1995 | Barthelemy et al. |
| 5,413,101 A | 5/1995 | Sugiura |
| 5,413,102 A | 5/1995 | Schmidt et al. |
| 5,417,207 A | 5/1995 | Young et al. |
| 5,421,329 A | 6/1995 | Casciani et al. |
| 5,425,360 A | 6/1995 | Nelson |
| 5,425,362 A | 6/1995 | Siker et al. |
| 5,427,093 A | 6/1995 | Ogawa et al. |
| 5,429,128 A | 7/1995 | Cadell et al. |
| 5,429,129 A | 7/1995 | Lovejoy et al. |
| 5,431,159 A | 7/1995 | Baker et al. |
| 5,431,170 A | 7/1995 | Mathews |
| 5,437,275 A | 8/1995 | Amundsen et al. |
| 5,438,986 A | 8/1995 | Disch et al. |
| 5,448,991 A | 9/1995 | Polson et al. |
| 5,452,717 A | 9/1995 | Branigan et al. |
| 5,465,714 A | 11/1995 | Scheuing |

| Patent | Kind | Date | Inventor |
|---|---|---|---|
| 5,469,845 | A | 11/1995 | DeLonzor et al. |
| RE35,122 | E | 12/1995 | Corenman et al. |
| 5,474,065 | A | 12/1995 | Meathrel et al. |
| 5,482,034 | A | 1/1996 | Lewis et al. |
| 5,482,036 | A | 1/1996 | Diab et al. |
| 5,483,646 | A | 1/1996 | Uchikoga |
| 5,485,847 | A | 1/1996 | Baker, Jr. |
| 5,490,505 | A | 2/1996 | Diab et al. |
| 5,490,523 | A | 2/1996 | Isaacson et al. |
| 5,491,299 | A | 2/1996 | Naylor et al. |
| 5,494,032 | A | 2/1996 | Robinson et al. |
| 5,497,771 | A | 3/1996 | Rosenheimer |
| 5,499,627 | A | 3/1996 | Steuer et al. |
| 5,503,148 | A | 4/1996 | Pologe et al. |
| 5,505,199 | A | 4/1996 | Kim |
| 5,507,286 | A | 4/1996 | Solenberger |
| 5,511,546 | A | 4/1996 | Hon |
| 5,517,988 | A | 5/1996 | Gerhard |
| 5,520,177 | A | 5/1996 | Ogawa et al. |
| 5,521,851 | A | 5/1996 | Wei et al. |
| 5,522,388 | A | 6/1996 | Ishikawa et al. |
| 5,524,617 | A | 6/1996 | Mannheimer |
| 5,529,064 | A | 6/1996 | Rall et al. |
| 5,533,507 | A | 7/1996 | Potratz et al. |
| 5,551,423 | A | 9/1996 | Sugiura |
| 5,551,424 | A | 9/1996 | Morrison et al. |
| 5,553,614 | A | 9/1996 | Chance |
| 5,553,615 | A | 9/1996 | Carim et al. |
| 5,555,882 | A | 9/1996 | Richardson et al. |
| 5,558,096 | A | 9/1996 | Palatnik |
| 5,560,355 | A | 10/1996 | Merchant et al. |
| 5,564,417 | A | 10/1996 | Chance |
| 5,575,284 | A | 11/1996 | Athan et al. |
| 5,575,285 | A | 11/1996 | Takanashi et al. |
| 5,577,500 | A | 11/1996 | Potratz |
| 5,582,169 | A | 12/1996 | Oda et al. |
| 5,584,296 | A | 12/1996 | Cui et al. |
| 5,588,425 | A | 12/1996 | Sackner et al. |
| 5,588,427 | A | 12/1996 | Tien |
| 5,590,652 | A | 1/1997 | Inai |
| 5,595,176 | A | 1/1997 | Yamaura |
| 5,596,986 | A | 1/1997 | Goldfarb |
| 5,611,337 | A | 3/1997 | Bukta |
| 5,617,852 | A | 4/1997 | MacGregor |
| 5,619,992 | A | 4/1997 | Guthrie et al. |
| 5,626,140 | A | 5/1997 | Feldman et al. |
| 5,630,413 | A | 5/1997 | Thomas et al. |
| 5,632,272 | A | 5/1997 | Diab et al. |
| 5,632,273 | A | 5/1997 | Suzuki |
| 5,634,459 | A | 6/1997 | Gardosi |
| 5,638,593 | A | 6/1997 | Gerhardt et al. |
| 5,638,818 | A | 6/1997 | Diab et al. |
| 5,645,060 | A | 7/1997 | Yorkey et al. |
| 5,645,440 | A | 7/1997 | Tobler et al. |
| 5,660,567 | A | 8/1997 | Nierlich et al. |
| 5,662,105 | A | 9/1997 | Tien |
| 5,662,106 | A | 9/1997 | Swedlow et al. |
| 5,666,952 | A | 9/1997 | Fuse et al. |
| 5,671,529 | A | 9/1997 | Nelson |
| 5,673,692 | A | 10/1997 | Schulze et al. |
| 5,673,693 | A | 10/1997 | Solenberger |
| 5,676,139 | A | 10/1997 | Goldberger et al. |
| 5,676,141 | A | 10/1997 | Hollub |
| 5,678,544 | A | 10/1997 | DeLonzor et al. |
| 5,680,857 | A | 10/1997 | Pelikan et al. |
| 5,685,299 | A | 11/1997 | Diab et al. |
| 5,685,301 | A | 11/1997 | Klomhaus |
| 5,687,719 | A | 11/1997 | Sato et al. |
| 5,687,722 | A | 11/1997 | Tien et al. |
| 5,692,503 | A | 12/1997 | Kuenstner |
| 5,692,505 | A | 12/1997 | Fouts |
| 5,709,205 | A | 1/1998 | Bukta |
| 5,713,355 | A | 2/1998 | Richardson et al. |
| 5,724,967 | A | 3/1998 | Venkatachalam |
| 5,727,547 | A | 3/1998 | Levinson et al. |
| 5,731,582 | A | 3/1998 | West |
| D393,830 | S | 4/1998 | Tobler et al. |
| 5,743,260 | A | 4/1998 | Chung et al. |
| 5,743,263 | A | 4/1998 | Baker, Jr. |
| 5,746,206 | A | 5/1998 | Mannheimer |
| 5,746,697 | A | 5/1998 | Swedlow et al. |
| 5,752,914 | A | 5/1998 | DeLonzor et al. |
| 5,755,226 | A | 5/1998 | Carim et al. |
| 5,758,644 | A | 6/1998 | Diab et al. |
| 5,760,910 | A | 6/1998 | Lepper, Jr. et al. |
| 5,766,125 | A | 6/1998 | Aoyagi et al. |
| 5,766,127 | A | 6/1998 | Pologe et al. |
| 5,769,785 | A | 6/1998 | Diab et al. |
| 5,772,587 | A | 6/1998 | Gratton et al. |
| 5,774,213 | A | 6/1998 | Trebino et al. |
| 5,776,058 | A | 7/1998 | Levinson et al. |
| 5,776,059 | A | 7/1998 | Kaestle |
| 5,779,630 | A | 7/1998 | Fein et al. |
| 5,779,631 | A | 7/1998 | Chance |
| 5,782,237 | A | 7/1998 | Casciani et al. |
| 5,782,756 | A | 7/1998 | Mannheimer |
| 5,782,757 | A | 7/1998 | Diab et al. |
| 5,782,758 | A | 7/1998 | Ausec et al. |
| 5,786,592 | A | 7/1998 | Hök |
| 5,790,729 | A | 8/1998 | Pologe et al. |
| 5,792,052 | A | 8/1998 | Isaacson et al. |
| 5,795,292 | A | 8/1998 | Lewis et al. |
| 5,797,841 | A | 8/1998 | DeLonzor et al. |
| 5,800,348 | A | 9/1998 | Kaestle |
| 5,800,349 | A | 9/1998 | Isaacson et al. |
| 5,803,910 | A | 9/1998 | Potratz |
| 5,807,246 | A | 9/1998 | Sakaguchi et al. |
| 5,807,247 | A | 9/1998 | Merchant et al. |
| 5,807,248 | A | 9/1998 | Mills |
| 5,810,723 | A | 9/1998 | Aldrich |
| 5,810,724 | A | 9/1998 | Gronvall |
| 5,813,980 | A | 9/1998 | Levinson et al. |
| 5,817,008 | A | 10/1998 | Rafert et al. |
| 5,817,009 | A | 10/1998 | Rosenheimer et al. |
| 5,817,010 | A | 10/1998 | Hibl |
| 5,818,985 | A | 10/1998 | Merchant et al. |
| 5,820,550 | A | 10/1998 | Polson et al. |
| 5,823,950 | A | 10/1998 | Diab et al. |
| 5,823,952 | A | 10/1998 | Levinson et al. |
| 5,827,182 | A | 10/1998 | Raley et al. |
| 5,830,135 | A | 11/1998 | Bosque et al. |
| 5,830,136 | A | 11/1998 | DeLonzor et al. |
| 5,830,137 | A | 11/1998 | Scharf |
| 5,839,439 | A | 11/1998 | Nierlich et al. |
| RE36,000 | E | 12/1998 | Swedlow et al. |
| 5,842,979 | A | 12/1998 | Jarman et al. |
| 5,842,981 | A | 12/1998 | Larsen et al. |
| 5,842,982 | A | 12/1998 | Mannheimer |
| 5,846,190 | A | 12/1998 | Woehrle |
| 5,851,178 | A | 12/1998 | Aronow |
| 5,851,179 | A | 12/1998 | Ritson et al. |
| 5,853,364 | A | 12/1998 | Baker, Jr. et al. |
| 5,860,919 | A | 1/1999 | Kiani-Azarbayjany et al. |
| 5,865,736 | A | 2/1999 | Baker, Jr. et al. |
| 5,871,442 | A | 2/1999 | Madarasz et al. |
| 5,879,294 | A | 3/1999 | Anderson et al. |
| 5,885,213 | A | 3/1999 | Richardson et al. |
| 5,890,929 | A | 4/1999 | Mills et al. |
| 5,891,021 | A | 4/1999 | Dillon et al. |
| 5,891,022 | A | 4/1999 | Pologe |
| 5,891,024 | A | 4/1999 | Jarman et al. |
| 5,891,025 | A | 4/1999 | Buschmann et al. |
| 5,891,026 | A | 4/1999 | Wang et al. |
| 5,902,235 | A | 5/1999 | Lewis et al. |
| 5,910,108 | A | 6/1999 | Solenberger |
| 5,911,690 | A | 6/1999 | Rall |
| 5,912,656 | A | 6/1999 | Tham et al. |
| 5,913,819 | A | 6/1999 | Taylor et al. |
| 5,916,154 | A | 6/1999 | Hobbs et al. |
| 5,916,155 | A | 6/1999 | Levinson et al. |
| 5,919,133 | A | 7/1999 | Taylor et al. |
| 5,919,134 | A | 7/1999 | Diab |
| 5,920,263 | A | 7/1999 | Huttenhoff et al. |
| 5,921,921 | A | 7/1999 | Potratz et al. |
| 5,922,607 | A | 7/1999 | Bernreuter |
| 5,924,979 | A | 7/1999 | Swedlow et al. |
| 5,924,980 | A | 7/1999 | Coetzee |
| 5,924,982 | A | 7/1999 | Chin |

| Patent No. | Kind | Date | Inventor |
|---|---|---|---|
| 5,924,985 | A | 7/1999 | Jones |
| 5,934,277 | A | 8/1999 | Mortz |
| 5,934,925 | A | 8/1999 | Tobler et al. |
| 5,940,182 | A | 8/1999 | Lepper, Jr. et al. |
| 5,954,644 | A | 9/1999 | Dettling et al. |
| 5,960,610 | A | 10/1999 | Levinson et al. |
| 5,961,450 | A | 10/1999 | Merchant et al. |
| 5,961,452 | A | 10/1999 | Chung et al. |
| 5,964,701 | A | 10/1999 | Asada et al. |
| 5,971,930 | A | 10/1999 | Elghazzawi |
| 5,978,691 | A | 11/1999 | Mills |
| 5,978,693 | A | 11/1999 | Hamilton et al. |
| 5,983,122 | A | 11/1999 | Jarman et al. |
| 5,987,343 | A | 11/1999 | Kinast |
| 5,991,648 | A | 11/1999 | Levin |
| 5,995,855 | A | 11/1999 | Kiani et al. |
| 5,995,856 | A | 11/1999 | Mannheimer et al. |
| 5,995,858 | A | 11/1999 | Kinast |
| 5,995,859 | A | 11/1999 | Takahashi |
| 5,997,343 | A | 12/1999 | Mills et al. |
| 5,999,834 | A | 12/1999 | Wang et al. |
| 6,002,952 | A | 12/1999 | Diab et al. |
| 6,005,658 | A | 12/1999 | Kaluza et al. |
| 6,006,120 | A | 12/1999 | Levin |
| 6,011,985 | A | 1/2000 | Athan et al. |
| 6,011,986 | A | 1/2000 | Diab et al. |
| 6,014,576 | A | 1/2000 | Raley et al. |
| 6,018,673 | A | 1/2000 | Chin et al. |
| 6,018,674 | A | 1/2000 | Aronow |
| 6,022,321 | A | 2/2000 | Amano et al. |
| 6,023,541 | A | 2/2000 | Merchant et al. |
| 6,026,312 | A | 2/2000 | Shemwell et al. |
| 6,026,314 | A | 2/2000 | Amerov et al. |
| 6,031,603 | A | 2/2000 | Fine et al. |
| 6,035,223 | A | 3/2000 | Baker, Jr. |
| 6,036,642 | A | 3/2000 | Diab et al. |
| 6,041,247 | A | 3/2000 | Weckstrom et al. |
| 6,044,283 | A | 3/2000 | Fein et al. |
| 6,047,201 | A | 4/2000 | Jackson, III |
| 6,061,584 | A | 5/2000 | Lovejoy et al. |
| 6,064,898 | A | 5/2000 | Aldrich |
| 6,064,899 | A | 5/2000 | Fein et al. |
| 6,067,462 | A | 5/2000 | Diab et al. |
| 6,073,038 | A | 6/2000 | Wang et al. |
| 6,078,833 | A | 6/2000 | Hueber |
| 6,081,735 | A | 6/2000 | Diab et al. |
| 6,081,742 | A | 6/2000 | Amano et al. |
| 6,083,157 | A | 7/2000 | Noller |
| 6,083,172 | A | 7/2000 | Baker, Jr. et al. |
| 6,088,607 | A | 7/2000 | Diab et al. |
| 6,094,592 | A | 7/2000 | Yorkey et al. |
| 6,095,974 | A | 8/2000 | Shemwell et al. |
| 6,104,938 | A | 8/2000 | Huiku et al. |
| 6,112,107 | A | 8/2000 | Hannula |
| 6,113,541 | A | 9/2000 | Dias et al. |
| 6,115,621 | A | 9/2000 | Chin |
| 6,122,535 | A | 9/2000 | Kaestle et al. |
| 6,133,994 | A | 10/2000 | Mathews et al. |
| 6,135,952 | A | 10/2000 | Coetzee |
| 6,144,444 | A | 11/2000 | Haworth et al. |
| 6,144,867 | A | 11/2000 | Walker et al. |
| 6,144,868 | A | 11/2000 | Parker |
| 6,149,481 | A | 11/2000 | Wang et al. |
| 6,150,951 | A | 11/2000 | Olejniczak |
| 6,151,107 | A | 11/2000 | Schöllermann et al. |
| 6,151,518 | A | 11/2000 | Hayashi |
| 6,152,754 | A | 11/2000 | Gerhardt et al. |
| 6,154,667 | A | 11/2000 | Miura et al. |
| 6,157,850 | A | 12/2000 | Diab et al. |
| 6,163,175 | A | 12/2000 | Larsen et al. |
| 6,163,715 | A | 12/2000 | Larsen et al. |
| 6,165,005 | A | 12/2000 | Mills et al. |
| 6,173,196 | B1 | 1/2001 | Delonzor et al. |
| 6,178,343 | B1 | 1/2001 | Bindszus et al. |
| 6,181,958 | B1 | 1/2001 | Steuer et al. |
| 6,181,959 | B1 | 1/2001 | Schöllermann et al. |
| 6,184,521 | B1 | 2/2001 | Coffin, IV et al. |
| 6,188,470 | B1 | 2/2001 | Grace |
| 6,192,260 | B1 | 2/2001 | Chance |
| 6,195,575 | B1 | 2/2001 | Levinson |
| 6,198,951 | B1 | 3/2001 | Kosuda et al. |
| 6,206,830 | B1 | 3/2001 | Diab et al. |
| 6,213,952 | B1 | 4/2001 | Finarov et al. |
| 6,217,523 | B1 | 4/2001 | Amano et al. |
| 6,222,189 | B1 | 4/2001 | Misner et al. |
| 6,226,539 | B1 | 5/2001 | Potratz |
| 6,226,540 | B1 | 5/2001 | Bernreuter et al. |
| 6,229,856 | B1 | 5/2001 | Diab et al. |
| 6,230,035 | B1 | 5/2001 | Aoyagi et al. |
| 6,233,470 | B1 | 5/2001 | Tsuchiya |
| 6,236,871 | B1 | 5/2001 | Tsuchiya |
| 6,236,872 | B1 | 5/2001 | Diab et al. |
| 6,240,305 | B1 | 5/2001 | Tsuchiya |
| 6,253,097 | B1 | 6/2001 | Aronow et al. |
| 6,253,098 | B1 | 6/2001 | Walker et al. |
| 6,256,523 | B1 | 7/2001 | Diab et al. |
| 6,256,524 | B1 | 7/2001 | Walker et al. |
| 6,261,236 | B1 | 7/2001 | Grimblatov |
| 6,263,221 | B1 | 7/2001 | Chance et al. |
| 6,263,222 | B1 | 7/2001 | Diab et al. |
| 6,263,223 | B1 | 7/2001 | Sheperd et al. |
| 6,266,546 | B1 | 7/2001 | Steuer et al. |
| 6,266,547 | B1 | 7/2001 | Walker et al. |
| 6,272,363 | B1 | 8/2001 | Casciani et al. |
| 6,278,522 | B1 | 8/2001 | Lepper, Jr. et al. |
| 6,280,213 | B1 | 8/2001 | Tobler et al. |
| 6,280,381 | B1 | 8/2001 | Malin et al. |
| 6,285,894 | B1 | 9/2001 | Oppelt et al. |
| 6,285,895 | B1 | 9/2001 | Ristolainen et al. |
| 6,285,896 | B1 | 9/2001 | Tobler et al. |
| 6,298,252 | B1 | 10/2001 | Kovach et al. |
| 6,308,089 | B1 | 10/2001 | Von der Ruhr et al. |
| 6,321,100 | B1 | 11/2001 | Parker |
| 6,330,468 | B1 | 12/2001 | Scharf |
| 6,334,065 | B1 | 12/2001 | Al-Ali et al. |
| 6,339,715 | B1 | 1/2002 | Bahr et al. |
| 6,343,223 | B1 | 1/2002 | Chin et al. |
| 6,343,224 | B1 | 1/2002 | Parker |
| 6,349,228 | B1 | 2/2002 | Kiani et al. |
| 6,351,658 | B1 | 2/2002 | Middleman et al. |
| 6,353,569 | B1 * | 3/2002 | Mizuno et al. ............ 365/210.1 |
| 6,353,750 | B1 | 3/2002 | Kimura et al. |
| 6,356,774 | B1 | 3/2002 | Bernstein et al. |
| 6,360,113 | B1 | 3/2002 | Dettling |
| 6,360,114 | B1 | 3/2002 | Diab et al. |
| 6,361,501 | B1 | 3/2002 | Amano et al. |
| 6,363,269 | B1 | 3/2002 | Hanna et al. |
| 6,370,408 | B1 | 4/2002 | Merchant et al. |
| 6,370,409 | B1 | 4/2002 | Chung et al. |
| 6,374,129 | B1 | 4/2002 | Chin et al. |
| 6,377,829 | B1 | 4/2002 | Al-Ali et al. |
| 6,381,479 | B1 | 4/2002 | Norris |
| 6,381,480 | B1 | 4/2002 | Stoddar et al. |
| 6,385,471 | B1 | 5/2002 | Mortz |
| 6,385,821 | B1 | 5/2002 | Modgil et al. |
| 6,388,240 | B2 | 5/2002 | Schulz et al. |
| 6,393,310 | B1 | 5/2002 | Kuenster |
| 6,397,091 | B2 | 5/2002 | Diab et al. |
| 6,397,092 | B1 | 5/2002 | Norris et al. |
| 6,397,093 | B1 | 5/2002 | Aldrich |
| 6,400,971 | B1 | 6/2002 | Finarov et al. |
| 6,400,972 | B1 | 6/2002 | Fine |
| 6,402,690 | B1 | 6/2002 | Rhee et al. |
| 6,408,198 | B1 | 6/2002 | Hanna et al. |
| 6,411,832 | B1 | 6/2002 | Guthermann |
| 6,411,833 | B1 | 6/2002 | Baker, Jr. et al. |
| 6,419,671 | B1 | 7/2002 | Lemberg |
| 6,421,549 | B1 | 7/2002 | Jacques |
| 6,430,423 | B2 | 8/2002 | DeLonzor et al. |
| 6,430,513 | B1 | 8/2002 | Wang et al. |
| 6,430,525 | B1 | 8/2002 | Weber et al. |
| 6,434,408 | B1 | 8/2002 | Heckel et al. |
| 6,438,399 | B1 | 8/2002 | Kurth |
| 6,449,501 | B1 | 9/2002 | Reuss |
| 6,453,183 | B1 | 9/2002 | Walker |
| 6,453,184 | B1 | 9/2002 | Hyogo et al. |
| 6,456,862 | B2 | 9/2002 | Benni |
| 6,461,305 | B1 | 10/2002 | Schnall |

| | | |
|---|---|---|
| 6,463,310 B1 | 10/2002 | Swedlow et al. |
| 6,463,311 B1 | 10/2002 | Diab |
| 6,466,808 B1 | 10/2002 | Chin et al. |
| 6,466,809 B1 | 10/2002 | Riley |
| 6,470,199 B1 | 10/2002 | Kopotic et al. |
| 6,470,200 B2 | 10/2002 | Walker et al. |
| 6,480,729 B2 | 11/2002 | Stone |
| 6,490,466 B1 | 12/2002 | Chew et al. |
| 6,496,711 B1 | 12/2002 | Athan et al. |
| 6,498,942 B1 | 12/2002 | Esenaliev et al. |
| 6,501,974 B1 | 12/2002 | Huiku |
| 6,501,975 B2 | 12/2002 | Diab et al. |
| 6,505,060 B1 | 1/2003 | Norris |
| 6,505,061 B2 | 1/2003 | Larson |
| 6,505,133 B1 | 1/2003 | Hanna et al. |
| 6,510,329 B2 | 1/2003 | Heckel |
| 6,510,331 B1 | 1/2003 | Williams et al. |
| 6,512,937 B2 | 1/2003 | Blank et al. |
| 6,515,273 B2 | 2/2003 | Al-Ali |
| 6,519,484 B1 | 2/2003 | Lovejoy et al. |
| 6,519,486 B1 | 2/2003 | Edgar, Jr. et al. |
| 6,519,487 B1 | 2/2003 | Parker |
| 6,525,386 B1 | 2/2003 | Mills et al. |
| 6,526,300 B1 | 2/2003 | Kiani et al. |
| 6,526,301 B2 | 2/2003 | Larsen et al. |
| 6,541,756 B2 | 4/2003 | Schulz et al. |
| 6,542,764 B1 | 4/2003 | Al-Ali et al. |
| 6,546,267 B1 | 4/2003 | Sugiura et al. |
| 6,553,241 B2 | 4/2003 | Mannheimer et al. |
| 6,553,242 B1 | 4/2003 | Sarussi |
| 6,553,243 B2 | 4/2003 | Gurley |
| 6,556,852 B1 | 4/2003 | Schulze et al. |
| 6,560,470 B1 | 5/2003 | Pologe |
| 6,564,077 B2 | 5/2003 | Mortara |
| 6,564,088 B1 | 5/2003 | Soller et al. |
| 6,571,113 B1 | 5/2003 | Fein et al. |
| 6,571,114 B1 | 5/2003 | Koike et al. |
| 6,574,491 B2 | 6/2003 | Elghazzawi |
| 6,580,086 B1 | 6/2003 | Schulz et al. |
| 6,584,336 B1 | 6/2003 | Ali et al. |
| 6,587,703 B2 | 7/2003 | Cheng et al. |
| 6,587,704 B1 | 7/2003 | Fine et al. |
| 6,589,172 B2 | 7/2003 | Williams et al. |
| 6,591,122 B2 | 7/2003 | Schmitt |
| 6,591,123 B2 | 7/2003 | Fein et al. |
| 6,594,511 B2 | 7/2003 | Stone et al. |
| 6,594,512 B2 | 7/2003 | Huang |
| 6,594,513 B1 | 7/2003 | Jobsis et al. |
| 6,597,931 B1 | 7/2003 | Cheng et al. |
| 6,597,933 B2 | 7/2003 | Kiani et al. |
| 6,600,940 B1 | 7/2003 | Fein et al. |
| 6,606,510 B2 | 8/2003 | Swedlow et al. |
| 6,606,511 B1 | 8/2003 | Ali et al. |
| 6,606,512 B2 | 8/2003 | Muz et al. |
| 6,615,064 B1 | 9/2003 | Aldrich |
| 6,615,065 B1 | 9/2003 | Barrett et al. |
| 6,618,602 B2 | 9/2003 | Levin et al. |
| 6,622,034 B1 | 9/2003 | Gorski et al. |
| 6,628,975 B1 | 9/2003 | Fein et al. |
| 6,631,281 B1 | 10/2003 | Kästle |
| 6,643,530 B2 | 11/2003 | Diab et al. |
| 6,643,531 B1 | 11/2003 | Katarow |
| 6,647,279 B2 | 11/2003 | Pologe |
| 6,647,280 B2 | 11/2003 | Bahr et al. |
| 6,650,917 B2 | 11/2003 | Diab et al. |
| 6,650,918 B2 | 11/2003 | Terry |
| 6,654,621 B2 | 11/2003 | Palatnik et al. |
| 6,654,622 B1 | 11/2003 | Eberhard et al. |
| 6,654,623 B1 | 11/2003 | Kästle |
| 6,654,624 B2 | 11/2003 | Diab et al. |
| 6,658,276 B2 | 12/2003 | Kianl et al. |
| 6,658,277 B2 | 12/2003 | Wasserman et al. |
| 6,662,033 B2 | 12/2003 | Casciani et al. |
| 6,665,551 B1 | 12/2003 | Suzuki |
| 6,668,182 B2 | 12/2003 | Hubelbank |
| 6,668,183 B2 | 12/2003 | Hicks et al. |
| 6,671,526 B1 | 12/2003 | Aoyagi et al. |
| 6,671,528 B2 | 12/2003 | Steuer et al. |
| 6,671,530 B2 | 12/2003 | Chung et al. |
| 6,671,531 B2 | 12/2003 | Al-Ali et al. |
| 6,671,532 B1 | 12/2003 | Fudge et al. |
| 6,675,031 B1 | 1/2004 | Porges et al. |
| 6,678,543 B2 | 1/2004 | Diab et al. |
| 6,681,126 B2 | 1/2004 | Solenberger |
| 6,681,128 B2 | 1/2004 | Steuer et al. |
| 6,681,454 B2 | 1/2004 | Modgil et al. |
| 6,684,090 B2 | 1/2004 | Ali et al. |
| 6,684,091 B2 | 1/2004 | Parker |
| 6,694,160 B2 | 2/2004 | Chin |
| 6,697,653 B2 | 2/2004 | Hanna |
| 6,697,655 B2 | 2/2004 | Sueppel et al. |
| 6,697,656 B1 | 2/2004 | Al-Ali |
| 6,697,658 B2 | 2/2004 | Al-Ali |
| RE38,476 E | 3/2004 | Diab et al. |
| 6,699,194 B1 | 3/2004 | Diab et al. |
| 6,699,199 B2 | 3/2004 | Asada et al. |
| 6,701,170 B2 | 3/2004 | Stetson |
| 6,702,752 B2 | 3/2004 | Dekker |
| 6,707,257 B2 | 3/2004 | Norris |
| 6,708,049 B1 | 3/2004 | Berson et al. |
| 6,709,402 B2 | 3/2004 | Dekker |
| 6,711,424 B1 | 3/2004 | Fine et al. |
| 6,711,425 B1 | 3/2004 | Reuss |
| 6,714,803 B1 | 3/2004 | Mortz |
| 6,714,804 B2 | 3/2004 | Al-Ali et al. |
| 6,714,805 B2 | 3/2004 | Jeon et al. |
| RE38,492 E | 4/2004 | Diab et al. |
| 6,719,686 B2 | 4/2004 | Coakley et al. |
| 6,719,705 B2 | 4/2004 | Mills |
| 6,720,734 B2 | 4/2004 | Norris |
| 6,721,584 B2 | 4/2004 | Baker, Jr. et al. |
| 6,721,585 B1 | 4/2004 | Parker |
| 6,725,074 B1 | 4/2004 | Kästle |
| 6,725,075 B2 | 4/2004 | Al-Ali |
| 6,731,963 B2 | 5/2004 | Finarov et al. |
| 6,731,967 B1 | 5/2004 | Turcott |
| 6,735,459 B2 | 5/2004 | Parker |
| 6,745,060 B2 | 6/2004 | Diab et al. |
| 6,745,061 B1 | 6/2004 | Hicks et al. |
| 6,748,253 B2 | 6/2004 | Norris et al. |
| 6,748,254 B2 | 6/2004 | O'Neill et al. |
| 6,754,515 B1 | 6/2004 | Pologe |
| 6,754,516 B2 | 6/2004 | Mannheimer |
| 6,760,607 B2 | 7/2004 | Al-Ali |
| 6,760,609 B2 | 7/2004 | Jacques |
| 6,760,610 B2 | 7/2004 | Tschupp et al. |
| 6,763,255 B2 | 7/2004 | DeLonzor et al. |
| 6,763,256 B2 | 7/2004 | Kimball et al. |
| 6,770,028 B1 | 8/2004 | Ali et al. |
| 6,771,994 B2 | 8/2004 | Kiani et al. |
| 6,773,397 B2 | 8/2004 | Kelly |
| 6,778,923 B2 | 8/2004 | Norris et al. |
| 6,780,158 B2 | 8/2004 | Yarita |
| 6,791,689 B1 | 9/2004 | Weckström |
| 6,792,300 B1 | 9/2004 | Diab et al. |
| 6,793,654 B2 | 9/2004 | Lemberg |
| 6,801,797 B2 | 10/2004 | Mannheimer et al. |
| 6,801,798 B2 | 10/2004 | Geddes et al. |
| 6,801,799 B2 | 10/2004 | Mendelson |
| 6,801,802 B2 | 10/2004 | Sitzman et al. |
| 6,802,812 B1 | 10/2004 | Walker et al. |
| 6,805,673 B2 | 10/2004 | Dekker |
| 6,810,277 B2 | 10/2004 | Edgar, Jr. et al. |
| 6,813,511 B2 | 11/2004 | Diab et al. |
| 6,816,741 B2 | 11/2004 | Diab |
| 6,819,950 B2 | 11/2004 | Mills |
| 6,822,564 B2 | 11/2004 | Al-Ali |
| 6,825,619 B2 | 11/2004 | Norris |
| 6,826,419 B2 | 11/2004 | Diab et al. |
| 6,829,496 B2 | 12/2004 | Nagai et al. |
| 6,830,711 B2 | 12/2004 | Mills et al. |
| 6,836,679 B2 | 12/2004 | Baker, Jr. et al. |
| 6,839,579 B1 | 1/2005 | Chin |
| 6,839,580 B2 | 1/2005 | Zonios et al. |
| 6,839,582 B2 | 1/2005 | Heckel |
| 6,839,659 B2 | 1/2005 | Tarassenko et al. |
| 6,842,635 B1 | 1/2005 | Parker |
| 6,845,256 B2 | 1/2005 | Chin et al. |

| | | |
|---|---|---|
| 6,850,787 B2 | 2/2005 | Weber et al. |
| 6,850,788 B2 | 2/2005 | Al-Ali |
| 6,850,789 B2 | 2/2005 | Schweitzer, Jr. et al. |
| 6,861,639 B2 | 3/2005 | Al-Ali |
| 6,863,652 B2 | 3/2005 | Huang et al. |
| 6,865,407 B2 | 3/2005 | Kimball et al. |
| 6,879,850 B2 | 4/2005 | Kimball |
| 6,882,874 B2 | 4/2005 | Huiku |
| 6,889,153 B2 | 5/2005 | Dietiker |
| 6,898,452 B2 | 5/2005 | Al-Ali et al. |
| 6,909,912 B2 | 6/2005 | Melker et al. |
| 6,912,413 B2 | 6/2005 | Rantala et al. |
| 6,916,289 B2 | 7/2005 | Schnall |
| 6,920,345 B2 | 7/2005 | Al-Ali et al. |
| 6,931,269 B2 | 8/2005 | Terry |
| 6,934,570 B2 | 8/2005 | Kiani et al. |
| 6,939,307 B1 | 9/2005 | Dunlop |
| 6,941,162 B2 | 9/2005 | Fudge et al. |
| 6,947,781 B2 | 9/2005 | Asada et al. |
| 6,950,687 B2 | 9/2005 | Al-Ali |
| 6,963,767 B2 | 11/2005 | Rantala et al. |
| 6,971,580 B2 | 12/2005 | DeLonzor et al. |
| 6,979,812 B2 | 12/2005 | Al-Ali et al. |
| 6,983,178 B2 | 1/2006 | Fine et al. |
| 6,985,763 B2 | 1/2006 | Boas et al. |
| 6,985,764 B2 | 1/2006 | Mason et al. |
| 6,990,426 B2 | 1/2006 | Yoon et al. |
| 6,992,751 B2 | 1/2006 | Al-Ali |
| 6,992,772 B2 | 1/2006 | Block et al. |
| 6,993,371 B2 | 1/2006 | Kiani et al. |
| 6,993,372 B2 | 1/2006 | Fine et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,006,855 B1 | 2/2006 | Sarussi |
| 7,006,856 B2 | 2/2006 | Baker, Jr. et al. |
| 7,016,715 B2 | 3/2006 | Stetson |
| 7,020,507 B2 | 3/2006 | Scharf et al. |
| 7,024,233 B2 | 4/2006 | Ali et al. |
| 7,024,235 B2 | 4/2006 | Melker et al. |
| 7,025,728 B2 | 4/2006 | Ito et al. |
| 7,027,849 B2 | 4/2006 | Al-Ali et al. |
| 7,027,850 B2 | 4/2006 | Wasserman |
| 7,035,697 B1 | 4/2006 | Brown |
| 7,039,449 B2 | 5/2006 | Al-Ali |
| 7,043,289 B2 | 5/2006 | Fine et al. |
| 7,047,055 B2 | 5/2006 | Boaz et al. |
| 7,047,056 B2 | 5/2006 | Hannula et al. |
| 7,060,035 B2 | 6/2006 | Wasserman et al. |
| 7,062,307 B2 | 6/2006 | Norris et al. |
| 7,067,893 B2 | 6/2006 | Mills et al. |
| 7,072,701 B2 | 7/2006 | Chen et al. |
| 7,072,702 B2 | 7/2006 | Edgar, Jr. et al. |
| 7,079,880 B2 | 7/2006 | Stetson |
| 7,085,597 B2 | 8/2006 | Fein et al. |
| 7,096,052 B2 | 8/2006 | Mason et al. |
| 7,096,054 B2 | 8/2006 | Abdul-Hafiz et al. |
| 7,107,088 B2 | 9/2006 | Aceti |
| 7,113,815 B2 | 9/2006 | O'Neil et al. |
| 7,123,950 B2 | 10/2006 | Mannheimer |
| 7,127,278 B2 | 10/2006 | Melker et al. |
| 7,130,671 B2 | 10/2006 | Baker, Jr. et al. |
| 7,132,641 B2 | 11/2006 | Schulz et al. |
| 7,133,711 B2 | 11/2006 | Chernoguz et al. |
| 7,139,559 B2 | 11/2006 | Terry |
| 7,142,901 B2 | 11/2006 | Kiani et al. |
| 7,162,288 B2 | 1/2007 | Nordstrom |
| 7,190,987 B2 | 3/2007 | Lindekugel et al. |
| 7,198,778 B2 | 4/2007 | Mannheimer et al. |
| 7,209,775 B2 | 4/2007 | Bae et al. |
| 7,215,984 B2 | 5/2007 | Diab et al. |
| 7,225,006 B2 | 5/2007 | Al-Ali et al. |
| 7,236,811 B2 | 6/2007 | Schmitt |
| 7,236,881 B2 | 6/2007 | Schmitt et al. |
| 7,248,910 B2 | 7/2007 | Li et al. |
| 7,254,433 B2 | 8/2007 | Diab et al. |
| 7,254,434 B2 | 8/2007 | Schulz et al. |
| 7,263,395 B2 | 8/2007 | Chan et al. |
| 7,272,425 B2 | 9/2007 | Al-Ali |
| 7,280,858 B2 | 10/2007 | Al-Ali et al. |
| 7,295,866 B2 | 11/2007 | Al-Ali et al. |
| 7,305,262 B2 | 12/2007 | Brodnick et al. |
| 7,315,753 B2 | 1/2008 | Baker, Jr. et al. |
| 7,371,981 B2 | 5/2008 | Abdul-Hafiz |
| 7,392,074 B2 | 6/2008 | Isaacson et al. |
| 7,428,432 B2 | 9/2008 | Ali et al. |
| 7,438,683 B2 | 10/2008 | Al-Ali et al. |
| 2001/0021803 A1 | 9/2001 | Blank et al. |
| 2001/0051767 A1 | 12/2001 | Williams et al. |
| 2002/0026109 A1 | 2/2002 | Diab et al. |
| 2002/0028990 A1 | 3/2002 | Sheperd et al. |
| 2002/0038078 A1 | 3/2002 | Ito |
| 2002/0042558 A1 | 4/2002 | Mendelson |
| 2002/0068859 A1 | 6/2002 | Knopp |
| 2002/0128544 A1 | 9/2002 | Diab et al. |
| 2002/0133067 A1 | 9/2002 | Jackson, III |
| 2002/0156354 A1 | 10/2002 | Larson |
| 2002/0173706 A1 | 11/2002 | Takatani |
| 2002/0173709 A1 | 11/2002 | Fine et al. |
| 2002/0190863 A1 | 12/2002 | Lynn |
| 2002/0198442 A1 | 12/2002 | Rantala et al. |
| 2003/0018243 A1 | 1/2003 | Gerhardt et al. |
| 2003/0036690 A1 | 2/2003 | Geddes et al. |
| 2003/0045785 A1 | 3/2003 | Diab et al. |
| 2003/0073889 A1 | 4/2003 | Keilbach et al. |
| 2003/0073890 A1 | 4/2003 | Hanna |
| 2003/0100840 A1 | 5/2003 | Sugiura et al. |
| 2003/0132495 A1 | 7/2003 | Mills et al. |
| 2003/0135099 A1 | 7/2003 | Al-Ali |
| 2003/0162414 A1 | 8/2003 | Schulz et al. |
| 2003/0171662 A1 | 9/2003 | O'Connor et al. |
| 2003/0176776 A1 | 9/2003 | Huiku |
| 2003/0181799 A1 | 9/2003 | Lindekugel et al. |
| 2003/0187337 A1 | 10/2003 | Tarassenko et al. |
| 2003/0195402 A1 | 10/2003 | Fein et al. |
| 2003/0197679 A1 | 10/2003 | Ali et al. |
| 2003/0212316 A1 | 11/2003 | Leiden et al. |
| 2003/0225323 A1 | 12/2003 | Kiani et al. |
| 2003/0225337 A1 | 12/2003 | Scharf et al. |
| 2003/0236452 A1 | 12/2003 | Melker et al. |
| 2003/0236647 A1 | 12/2003 | Yoon et al. |
| 2004/0006261 A1 | 1/2004 | Swedlow et al. |
| 2004/0010188 A1 | 1/2004 | Wasserman et al. |
| 2004/0024297 A1 | 2/2004 | Chen et al. |
| 2004/0024326 A1 | 2/2004 | Yeo et al. |
| 2004/0034293 A1 | 2/2004 | Kimball |
| 2004/0039272 A1 | 2/2004 | Abdul-Hafiz et al. |
| 2004/0039273 A1 | 2/2004 | Terry |
| 2004/0054269 A1 | 3/2004 | Rantala et al. |
| 2004/0054291 A1 | 3/2004 | Schulz et al. |
| 2004/0059209 A1 | 3/2004 | Al-Ali et al. |
| 2004/0059210 A1 | 3/2004 | Stetson |
| 2004/0064020 A1 | 4/2004 | Diab et al. |
| 2004/0068164 A1 | 4/2004 | Diab et al. |
| 2004/0087846 A1 | 5/2004 | Wasserman |
| 2004/0092805 A1 | 5/2004 | Yarita |
| 2004/0097797 A1 | 5/2004 | Porges et al. |
| 2004/0098009 A1 | 5/2004 | Boecker et al. |
| 2004/0107065 A1 | 6/2004 | Al-Ali et al. |
| 2004/0116788 A1 | 6/2004 | Chernoguz et al. |
| 2004/0116789 A1 | 6/2004 | Boaz et al. |
| 2004/0117891 A1 | 6/2004 | Hannula et al. |
| 2004/0122300 A1 | 6/2004 | Boas et al. |
| 2004/0122302 A1 | 6/2004 | Mason et al. |
| 2004/0133087 A1 | 7/2004 | Ali et al. |
| 2004/0133088 A1 | 7/2004 | Al-Ali et al. |
| 2004/0138538 A1 | 7/2004 | Stetson |
| 2004/0138540 A1 | 7/2004 | Baker, Jr. et al. |
| 2004/0143172 A1 | 7/2004 | Fudge et al. |
| 2004/0147821 A1 | 7/2004 | Al-Ali et al. |
| 2004/0147822 A1 | 7/2004 | Al-Ali et al. |
| 2004/0147823 A1 | 7/2004 | Kiani et al. |
| 2004/0147824 A1 | 7/2004 | Diab et al. |
| 2004/0152965 A1 | 8/2004 | Diab et al. |
| 2004/0158134 A1 | 8/2004 | Diab et al. |
| 2004/0158135 A1 | 8/2004 | Baker, Jr. et al. |
| 2004/0162472 A1 | 8/2004 | Berson et al. |

| | | |
|---|---|---|
| 2004/0171920 A1 | 9/2004 | Mannheimer et al. |
| 2004/0171948 A1 | 9/2004 | Terry |
| 2004/0176671 A1 | 9/2004 | Fine et al. |
| 2004/0181133 A1 | 9/2004 | Al-Ali et al. |
| 2004/0181134 A1 | 9/2004 | Baker, Jr. et al. |
| 2004/0186358 A1 | 9/2004 | Chernow et al. |
| 2004/0199063 A1 | 10/2004 | O'Neil et al. |
| 2004/0204636 A1 | 10/2004 | Diab et al. |
| 2004/0204637 A1 | 10/2004 | Diab et al. |
| 2004/0204638 A1 | 10/2004 | Diab et al. |
| 2004/0204639 A1 | 10/2004 | Casciani et al. |
| 2004/0204865 A1 | 10/2004 | Lee et al. |
| 2004/0210146 A1 | 10/2004 | Diab et al. |
| 2004/0215069 A1 | 10/2004 | Mannheimer |
| 2004/0230107 A1 | 11/2004 | Asada et al. |
| 2004/0230108 A1 | 11/2004 | Melker et al. |
| 2004/0236196 A1 | 11/2004 | Diab et al. |
| 2004/0242980 A1 | 12/2004 | Kiani et al. |
| 2004/0249252 A1 | 12/2004 | Fine et al. |
| 2004/0257557 A1 | 12/2004 | Block et al. |
| 2004/0260161 A1 | 12/2004 | Melker et al. |
| 2004/0267103 A1 | 12/2004 | Li et al. |
| 2004/0267104 A1 | 12/2004 | Hannula et al. |
| 2004/0267140 A1 | 12/2004 | Ito et al. |
| 2005/0004479 A1 | 1/2005 | Townsend et al. |
| 2005/0010092 A1 | 1/2005 | Weber et al. |
| 2005/0020887 A1 | 1/2005 | Goldberg |
| 2005/0020894 A1 | 1/2005 | Norris et al. |
| 2005/0033128 A1 | 2/2005 | Ali et al. |
| 2005/0033129 A1 | 2/2005 | Edgar, Jr. et al. |
| 2005/0043599 A1 | 2/2005 | O'Mara |
| 2005/0043600 A1 | 2/2005 | Diab et al. |
| 2005/0049470 A1 | 3/2005 | Terry |
| 2005/0049471 A1 | 3/2005 | Aceti |
| 2005/0065417 A1 | 3/2005 | Ali et al. |
| 2005/0075550 A1 | 4/2005 | Lindekugel |
| 2005/0101848 A1 | 5/2005 | Al-Ali et al. |
| 2005/0113651 A1 | 5/2005 | Wood et al. |
| 2005/0177034 A1 | 8/2005 | Beaumont |
| 2005/0192488 A1 | 9/2005 | Bryenton et al. |
| 2005/0197548 A1 | 9/2005 | Dietiker |
| 2005/0228248 A1 | 10/2005 | Dietiker |
| 2005/0277819 A1 | 12/2005 | Kiani et al. |
| 2005/0283059 A1 | 12/2005 | Iyer et al. |
| 2006/0025660 A1 | 2/2006 | Swedlow et al. |
| 2006/0030762 A1 | 2/2006 | Swedlow et al. |
| 2006/0030763 A1 | 2/2006 | Mannheimer et al. |
| 2006/0030764 A1 | 2/2006 | Porges et al. |
| 2006/0030765 A1 | 2/2006 | Swedlow et al. |
| 2006/0058594 A1 | 3/2006 | Ishizuka et al. |
| 2006/0084852 A1 | 4/2006 | Mason et al. |
| 2006/0089547 A1 | 4/2006 | Sarussi |
| 2006/0106294 A1 | 5/2006 | Maser et al. |
| 2006/0195028 A1 | 8/2006 | Hannula et al. |
| 2006/0200018 A1 | 9/2006 | Al-Ali |
| 2006/0211925 A1 | 9/2006 | Lamego et al. |
| 2006/0211932 A1 | 9/2006 | Al-Ali et al. |
| 2006/0217604 A1 | 9/2006 | Fein et al. |
| 2006/0217605 A1 | 9/2006 | Fein et al. |
| 2006/0217606 A1 | 9/2006 | Fein et al. |
| 2006/0217607 A1 | 9/2006 | Fein et al. |
| 2006/0217608 A1 | 9/2006 | Fein et al. |
| 2006/0224058 A1 | 10/2006 | Mannheimer |
| 2006/0229510 A1 | 10/2006 | Fein et al. |
| 2006/0229511 A1 | 10/2006 | Fein et al. |
| 2006/0247501 A1 | 11/2006 | Ali |
| 2006/0258921 A1 | 11/2006 | Addison et al. |
| 2006/0258926 A1 | 11/2006 | Ali et al. |
| 2006/0276700 A1 | 12/2006 | O'Neil |
| 2007/0032710 A1 | 2/2007 | Raridan et al. |
| 2007/0032712 A1 | 2/2007 | Raridan et al. |
| 2007/0032715 A1 | 2/2007 | Eghbal et al. |
| 2007/0043269 A1 | 2/2007 | Mannheimer et al. |
| 2007/0043270 A1 | 2/2007 | Mannheimer et al. |
| 2007/0043271 A1 | 2/2007 | Mannheimer et al. |
| 2007/0043272 A1 | 2/2007 | Mannheimer et al. |
| 2007/0043273 A1 | 2/2007 | Mannheimer et al. |
| 2007/0043274 A1 | 2/2007 | Mannheimer et al. |
| 2007/0043275 A1 | 2/2007 | Mannheimer et al. |
| 2007/0043276 A1 | 2/2007 | Mannheimer et al. |
| 2007/0043277 A1 | 2/2007 | Mannheimer et al. |
| 2007/0043278 A1 | 2/2007 | Mannheimer et al. |
| 2007/0043279 A1 | 2/2007 | Mannheimer et al. |
| 2007/0043280 A1 | 2/2007 | Mannheimer et al. |
| 2007/0043282 A1 | 2/2007 | Mannheimer et al. |
| 2007/0073116 A1 | 3/2007 | Kiani et al. |
| 2007/0073121 A1 | 3/2007 | Hoarau et al. |
| 2007/0073125 A1 | 3/2007 | Hoarau et al. |
| 2007/0073126 A1 | 3/2007 | Raridan, Jr. |
| 2007/0073127 A1 | 3/2007 | Kiani et al. |
| 2007/0073128 A1 | 3/2007 | Hoarau et al. |
| 2007/0088207 A1 | 4/2007 | Mannheimer et al. |
| 2007/0100220 A1 | 5/2007 | Baker et al. |
| 2007/0123756 A1 | 5/2007 | Kitajima et al. |
| 2007/0244376 A1 | 10/2007 | Wang |
| 2008/0039701 A1 | 2/2008 | Ali |
| 2008/0081969 A1 | 4/2008 | Feldman et al. |
| 2008/0081970 A1 | 4/2008 | Boyce et al. |
| 2008/0088467 A1 | 4/2008 | Al-Ali |
| 2008/0221413 A1 | 9/2008 | Hoarau |
| 2008/0221462 A1 | 9/2008 | Baker |

FOREIGN PATENT DOCUMENTS

| | | |
|---|---|---|
| JP | 27117641 | 5/2007 |
| JP | 27190122 | 8/2007 |
| WO | WO03011127 | 2/2003 |
| WO | 2010001231 A2 | 1/2010 |

* cited by examiner

SYSTEM AND METHOD FOR MEMORY SWITCHING FOR MULTIPLE CONFIGURATION MEDICAL SENSOR

BACKGROUND

The present disclosure relates generally to medical devices and, more particularly, to sensors used for sensing physiological parameters of a patient.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the field of medicine, doctors often desire to monitor certain physiological characteristics of their patients. Accordingly, a wide variety of devices have been developed for monitoring many such physiological characteristics. Such devices provide doctors and other healthcare personnel with the information they need to provide the best possible healthcare for their patients. As a result, such monitoring devices have become an indispensable part of modern medicine.

One technique for monitoring certain physiological characteristics of a patient is commonly referred to as pulse oximetry, and the devices built based upon pulse oximetry techniques are commonly referred to as pulse oximeters. Pulse oximetry may be used to measure various blood flow characteristics, such as the blood-oxygen saturation of hemoglobin in arterial blood, the volume of individual blood pulsations supplying the tissue, and/or the rate of blood pulsations corresponding to each heartbeat of a patient. In fact, the "pulse" in pulse oximetry refers to the time varying amount of arterial blood in the tissue during each cardiac cycle.

Pulse oximeters typically utilize a non-invasive sensor that transmits light through a patient's tissue and that photoelectrically detects the absorption and/or scattering of the transmitted light in such tissue. One or more of the above physiological characteristics may then be calculated based upon the amount of light absorbed and/or scattered. More specifically, the light passed through the tissue is typically selected to be of one or more wavelengths that may be absorbed and/or scattered by the blood in an amount correlative to the amount of the blood constituent present in the blood. The amount of light absorbed and/or scattered may then be used to estimate the amount of blood constituent in the tissue using various algorithms. This determination may be performed in a monitor coupled to the sensor that receives the necessary data for the blood constituent calculation.

Some sensors may be capable of application to multiple placement sites on a patient's body. For example, sensors may be placed on a patient's forehead, a patient's digit, etc. To determine the amount of constituent based on the sensor data, the monitor coupled to the sensor may use specific algorithms for each placement site and sensor configuration. However, some monitors may not include the calibration data for such sensors. Additionally, older monitors may be incompatible with multiple configuration sensors and may not include calibration data or the ability to select calibration data based on the sensor configuration and/or placement site.

Certain aspects commensurate in scope with the disclosure are set forth below. It should be understood that these aspects are presented merely to provide the reader with a brief summary of certain forms of the disclosure might take and that these aspects are not intended to limit the scope of the disclosure. Indeed, the disclosure may encompass a variety of aspects that may not be set forth below.

In one embodiment, there is provided a system having a monitor, a sensor, and a sensor connector. The sensor includes a sensor body having a first configuration adapted to be applied to a first tissue site and a second configuration adapted to be applied to a second tissue site and is configured to measure a physiological characteristic. The sensor connector is coupled to the monitor and the sensor and includes a first memory device storing a first set of calibration data, a second memory device storing a second set of calibration data, such that first memory device is accessible by the monitor in the first configuration and the second memory device is accessible by the monitor in the second configuration.

In another embodiment, there is provided a sensor connector for a medical sensor having a first memory device, a second memory device, such that the first memory device is electrically accessible in a first configuration of a sensor coupled to the sensor connector and the second memory device is electrically accessible in a second configuration of the sensor.

Another embodiment includes a system having a sensor and a sensor connector. The sensor includes a sensor body having a first configuration adapted to be applied to a first tissue site and a second configuration adapted to be applied to a second tissue site and is configured to measure a physiological parameter. The sensor also includes a first conductive trace disposed within the sensor body, wherein the first conductive trace is intact in the first configuration and broken in the second configuration. Additionally, the sensor includes a second conductive trace disposed within the sensor body, wherein the second conductive trace is intact in the first configuration and broken in the second configuration. The sensor connector is coupled to the sensor and includes a first memory device coupled to the first conductive trace and a second memory device coupled to the second conductive trace, such that the first memory device is electrically accessible in a first configuration of a sensor coupled to the sensor connector and the second memory device is electrically accessible in a second configuration of the sensor.

Another embodiment is provided that includes a system that includes a monitor, a sensor coupled to the monitor, and a sensor adaptor coupled between the monitor and the sensor. The sensor comprises a sensor body having a first configuration adapted to be applied to a first tissue site and a second configuration adapted to be applied to a second tissue site and is adapted to measure a physiological parameter. The sensor also includes a memory device storing a first set of calibration data for the first configuration and a second set of calibration data for the second configuration. The sensor adaptor includes a processing circuit configured to provide the first set of calibration data to the monitor in the first configuration and provide the second set of calibration data to the monitor in the second configuration.

Yet another embodiment includes a sensor adaptor that includes a processing circuit configured to provide a first set of calibration data from a sensor memory to a monitor for first configuration of the sensor and provide a second set of calibration data from the sensor memory to the monitor for the second configuration of the sensor.

BRIEF DESCRIPTION OF THE DRAWINGS

Advantages of the disclosed techniques may become apparent upon reading the following detailed description and upon reference to the drawings in which.

DETAILED DESCRIPTION OF SPECIFIC EMBODIMENTS

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Figure 1:
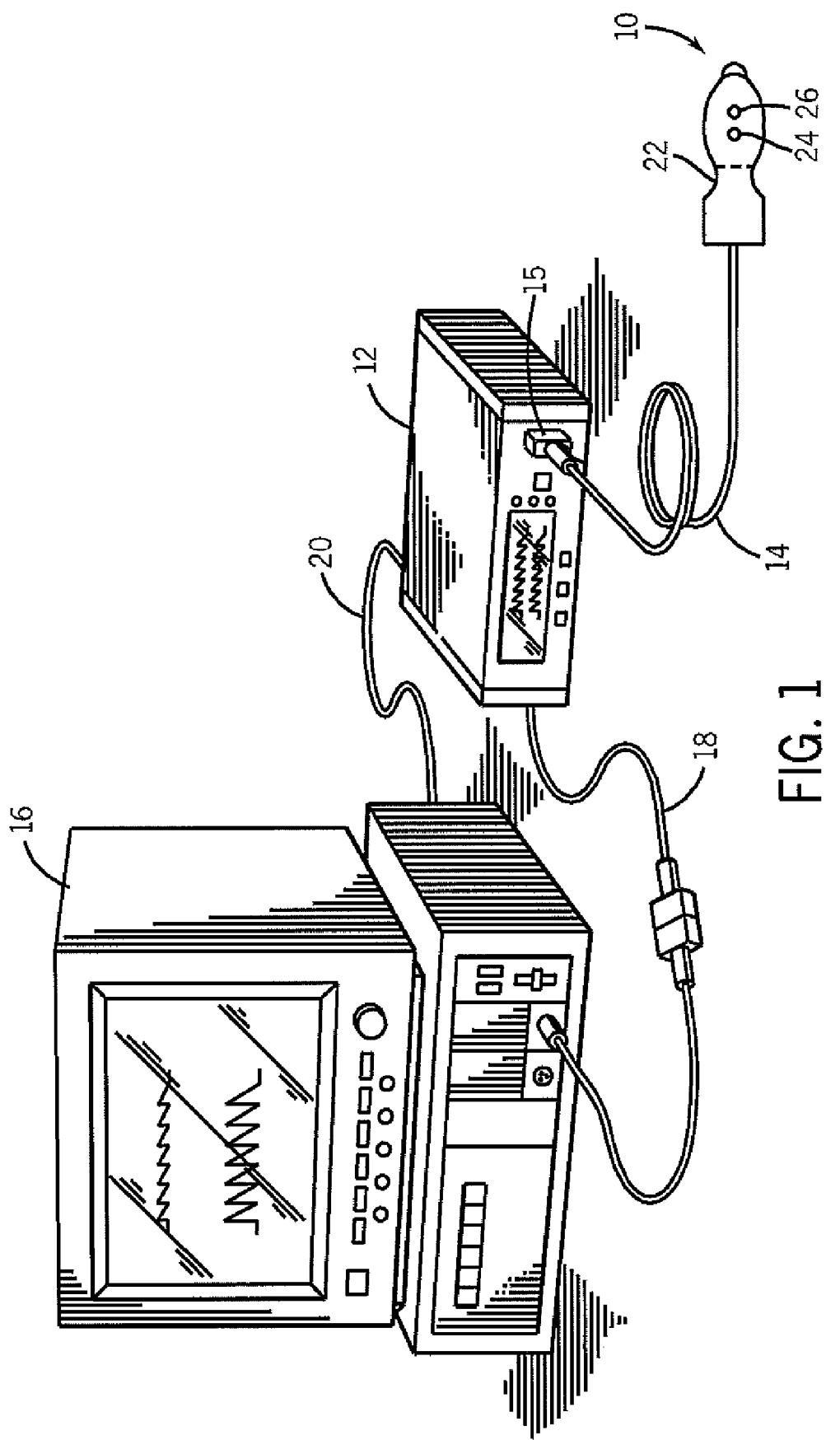
FIG. 1 illustrates a system coupled to a multi-parameter patient monitor and a sensor in accordance with an embodiment of the present disclosure.

FIG. 1 depicts a multi-configuration sensor 10 that may be used in conjunction with a monitor 12 in accordance with an embodiment of the present disclosure. The sensor 10 may be coupled to the monitor 12 via sensor cable 14 and sensor connector 15, or the sensor 10 may be coupled to a transmission device (not shown) to facilitate wireless transmission between the sensor 10 and the monitor 12. The monitor 12 may be any suitable pulse oximeter, such as those available from Nellcor Puritan Bennett, LLC. Furthermore, to upgrade conventional operation provided by the monitor 12 to provide additional functions, the monitor 12 may be coupled to a multi-parameter patient monitor 16 via a cable 18 connected to a sensor input port or via a cable 20 connected to a digital communication port, or through wireless transmission components (not shown).

The sensor 10 may be a multiple configuration sensor capable of being applied to a multiple placement sites (e.g., multiple tissue sites such as a patient's finger, a patient's forehead, etc.) as described further in U.S. patent application Ser. No. 11/716,770, which is hereby incorporated by reference in its entirety. The sensor 10 may include a sensor body 22 includes an emitter 24 and a detector 26 disposed on its surface. As depicted, the emitter 24 and detector 26 may be arranged in a reflectance-type configuration in which the emitter 24 and detector 26 that are typically placed on the same side of the sensor site. Reflectance type sensors may operate by emitting light into the tissue and detecting the light that is transmitted and scattered by the tissue. Reflectance type sensors detect light photons that are scattered back to the detector 26.

Figure 2:
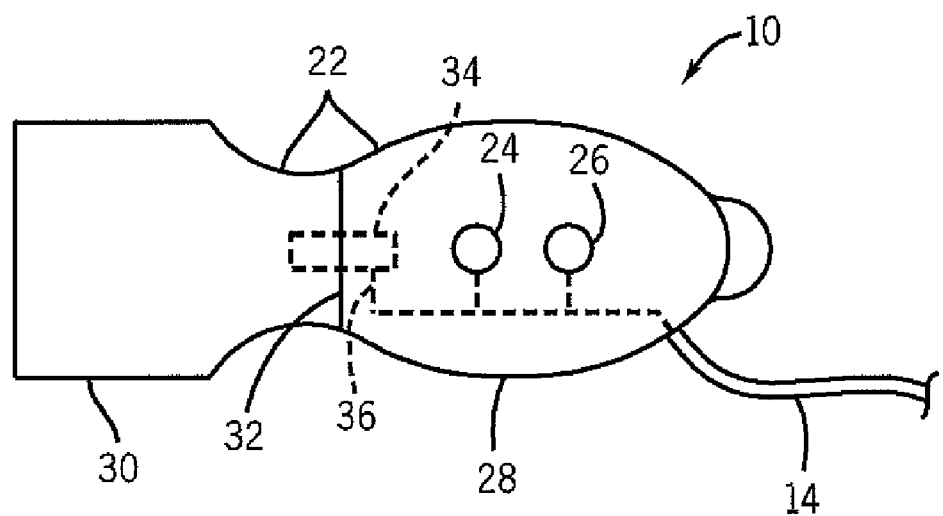
FIG. 2 depicts is a multiple configuration medical sensor having a breakable conductive trace in accordance with an embodiment of the present disclosure.

Turning now in more detail to the sensor 10 as further illustrated in FIG. 2, the sensor body 22 may include a detecting portion 28 that includes the emitter 24 and the detector 26 and any electrical connectors, such as wire leads, that may operatively connect the emitter 24 and the detector 26 to the cable 14, which may be connected to a downstream monitoring device. The sensor body 22 may also include a removable portion 30 that may be separated from the detecting portion 28 by a perforation 32. The detecting portion 28 and the removable portion 30 of the sensor body 22 may be wrapped around a patient's digit to achieve a substantially conforming and secure fit. The removable portion 30 provides additional surface area that allows the sensor body 22 to be able to wrap around the digit, which may provide a more secure fit for the sensor 10. The sensor 10 may also include an adhesive layer (not shown) in order to enhance the sensor's fit to the tissue.

The sensor 10 may also include an indicator circuit, such as conductive trace 34, which is closed when the removable portion 30 is still attached to the detecting portion 28. The conductive trace 34 may be disposed on the sensor body 22 such that a portion of the trace 34 is on the removable portion 30 and a portion of the trace 34 is on the detecting portion 28. When the removable portion 30 is separated from the detecting portion 28, the trace is broken (see FIG. 3). As described in detail below, the electrical continuity (intact conductive trace) or electrical discontinuity (broken conductive trace) of the conductive trace 34 may be used to alternate accessibility of multiple memory devices of the sensor 10. The electrical continuity (or discontinuity) of the conductive trace 34 may be detected via wire leads 36. The intact conductive trace 34 may be indicative of a first configuration of the sensor 10, e.g., a configuration suitable for application to a first placement site such as a patient's digit. The conductive trace 34 and the leads 36 may include one or more conductive portions, as described in detail below. For example, the leads 36 may include multiple conductive portions coupled to the trace 34 to enable detection of electrical continuity and discontinuity across the conductive trace 34.

Figure 3:
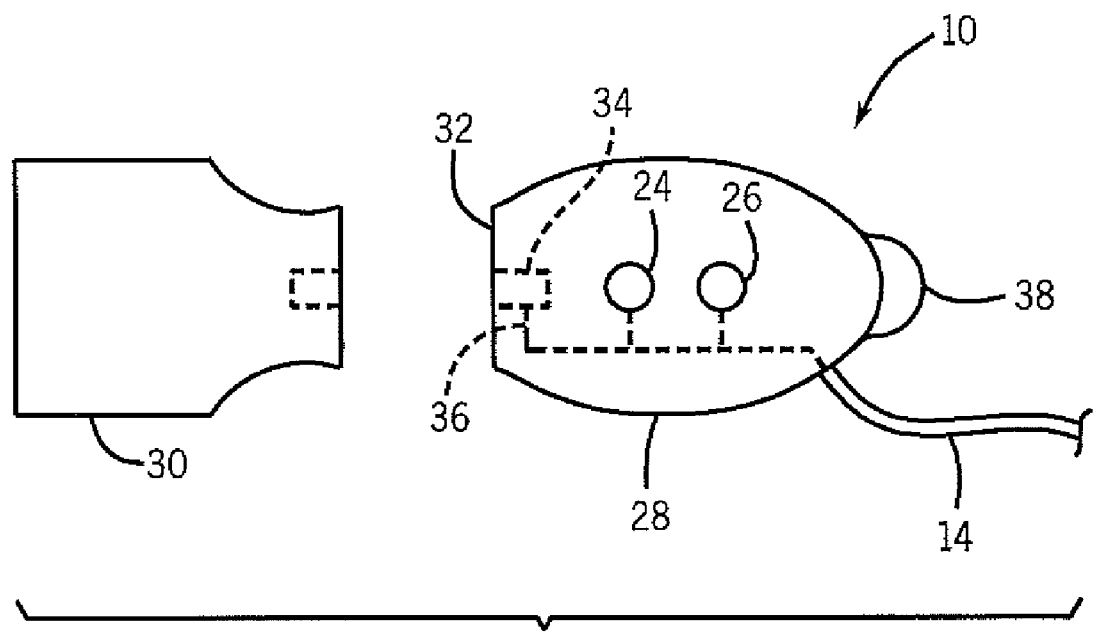
FIG. 3 depicts the sensor of FIG. 2 in a second configuration having a broken conductive trace in accordance with an embodiment of the present disclosure.

As shown in FIG. 3, when the removable portion 30 is detached from the detecting portion 28, the conductive trace 34 is broken. As shown, the detecting portion 28 retains the ability to measure a physiological parameter because the emitter 24, the detector 26, and the cable 14 are all included in the detecting portion 28 while being configured to have a smaller surface area that may be more appropriate for use on a different tissue site, such as a forehead, an ear, or a foot. The broken conductive trace 34 may be indicative of a second configuration of the sensor 10, e.g., a configuration suitable for application to a first placement site such as a patient's digit.

In certain embodiments, the detecting portion 28 may be removed from the removable portion 30 through tearing along the perforation line 32. In other embodiments, the removable portion 30 may be cut away from the detecting portion 28. After removal of the removable portion 30, the detecting portion 28 of the sensor 10 may be placed on another sensor placement site, e.g., a patient's forehead. The detecting portion 28 may also include additional portions, such as a flap 38, which may assist in the placement and/or removal of the detecting portion 28 from the patient's forehead. In other embodiments, a sensor may be configured such that the transition between a first configuration and a second configuration may be achieved through bending or folding the sensor body rather than removing a portion of the sensor body. Further, in some embodiments the sensor configurations may be reversible, such that the removable portion 30 may be reconnected to the detecting portion 28, reestablishing the continuity of the conductive trace 34.

Figure 4:
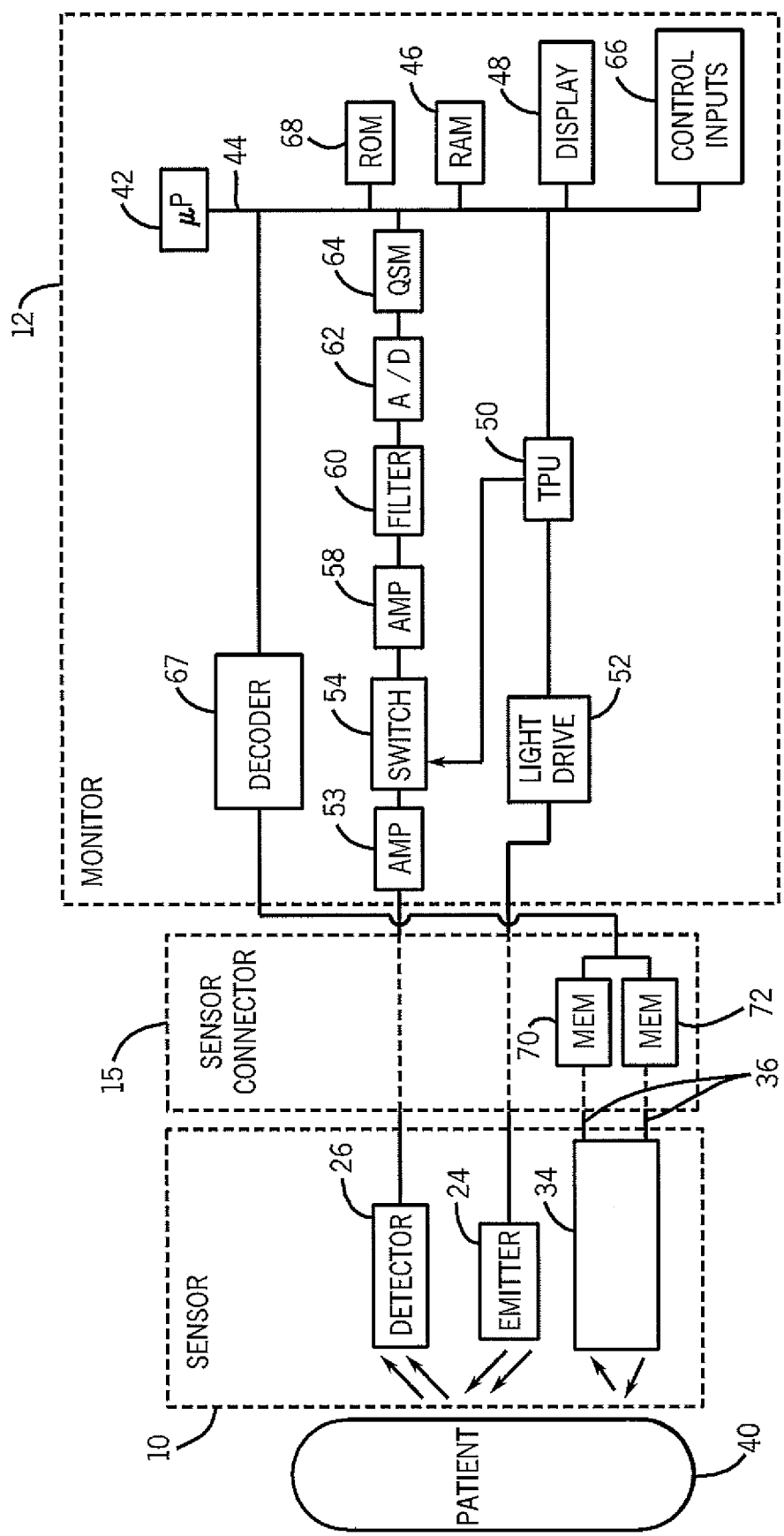
FIG. 4 is a block diagram of the monitor connected to the sensor of FIGS. 1-3 in accordance with an embodiment of the present disclosure.

FIG. 4 is a block diagram of the monitor 12 connected to the sensor 10 by the sensor connector 15 in accordance with an embodiment of the present disclosure. The monitor 12 may be a pulse oximeter monitor or any monitor capable of determining any suitable physiological parameter from the data received from the sensor 10. For example, light from emitter 24 passes into a blood perfused tissue 40, and is scattered and detected by detector 26. The sensor 10 may also include the conductive trace 34 as described and may be configured to provide the electrically continuity of the conductive trace 34 to the sensor connector 15 via wire leads 36.

The monitor 12 may include a microprocessor 42 connected to an internal bus 44. In this embodiment, also connected to the bus are a RAM memory 46 and a display 48. A time processing unit (TPU) 50 may provide timing control signals to light drive circuitry 52 which controls when the emitter 24 is illuminated, and if multiple light sources are used, the multiplexed timing for the different light sources. TPU 50 may also control the gating-in of signals from detector 26 through an amplifier 53 and a switching circuit 56. These signals are sampled at the proper time, depending upon which of multiple light sources is illuminated, if multiple light sources are used. The received signal from the detector 26 may be passed through an amplifier 58, a low pass filter 60, and an analog-to-digital converter 62. The digital data is may then be stored in a queued serial module (QSM) 64, for later downloading to RAM 46 as QSM 64 fills up. In one embodiment, there may be multiple parallel paths of separate amplifier, filter and A/D converters for multiple light wavelengths or spectra received. The monitor 12 may include control inputs 66 such as a switch, dial, buttons, a keyboard, a mouse, a trackball, or a port providing instructions from a remote host computer.

The monitor 12 may be configured to receive signals from the sensor 10 related to a physiological constituent that may be processed by the monitor 12 determine a physiological parameter. The monitor 12 may be configured to provide an indication about the sensor condition, such as an audio indicator, visual indicator or a display message. Further, the monitor 12 may include a decoder 67 to receive information about the sensor 10 from a memory device. Such a device may include a code or other identification parameter that may allow the monitor 12 to select an appropriate software or hardware instruction, which may include calibration coefficients for the emitter 24 and/or the detector 26, for processing the signal.

Based on the value of the received signals corresponding to the light received by detector 26, microprocessor 42 will calculate a physiological parameter using various algorithms. These algorithms may use calibration data, such as calibration coefficients, which may be empirically determined, corresponding to, for example, the wavelengths of light used, the type of sensor, and the placement site of the sensor 10. Furthermore, any number of methods or algorithms may be used to determine a patient's pulse rate, oxygen saturation or any other desired physiological parameter. In some embodiments, calibration data may be stored in a read-only memory (ROM) 68.

In some embodiments, the monitor 12 may be configured receive calibration data from a device, such as data stored in a memory device and decoded by the decoder 67. As shown in FIG. 4, the sensor connector 15 may include a first memory device 70 (e.g., a memory chip) and a second memory device 72 (e.g., a second memory chip) In such an embodiment, the first memory device 70 may store calibration data corresponding to the first configuration of the sensor 10 and the first placement site (e.g., a digit). Similarly, the second memory device 72 may store calibration data corresponding to the second configuration of the sensor 10 and the second placement site (e.g., a forehead). However, in such an embodiment, the monitor 12 may not be configured to read and interpret calibration data stored in multiple memory devices. For example, older monitors or monitors not configured to operate with multiple configuration sensors such as sensor 10 may not detect or read the appropriate memory device for a given sensor configuration.

As illustrated and discussed further below in FIGS. 5-9, the electrical continuity/discontinuity of the conductive trace 34 may used to determine which memory device 70 or 72 is used and read by the monitor 12. Additional information may be stored in the memory devices 70 and 72 and provided to the monitor, such as alternative placement sites for the current sensor configuration, messages used by the monitor 12, etc. Each of FIGS. 5-9 described below describe embodiments of memory switching configurations that may be used by sensor connector 15.

Figure 5A:
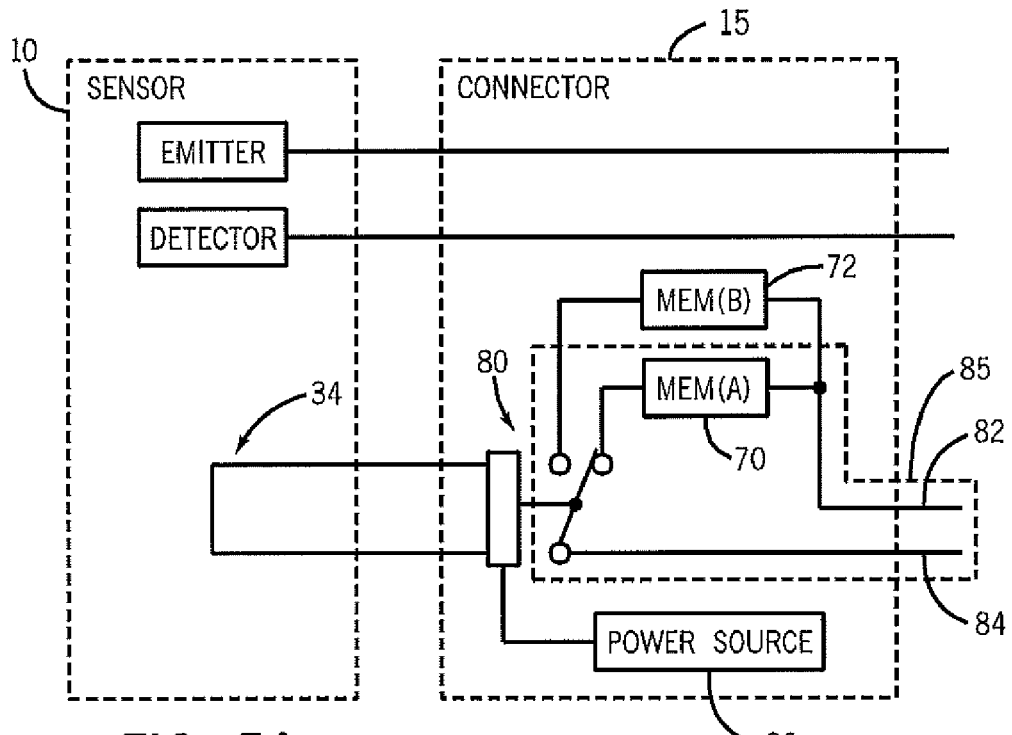
FIGS. 5A and 5B are block diagrams of a sensor and sensor connector having switchable memory devices coupled to a switch in accordance with an embodiment of the present disclosure.
Figure 5B:
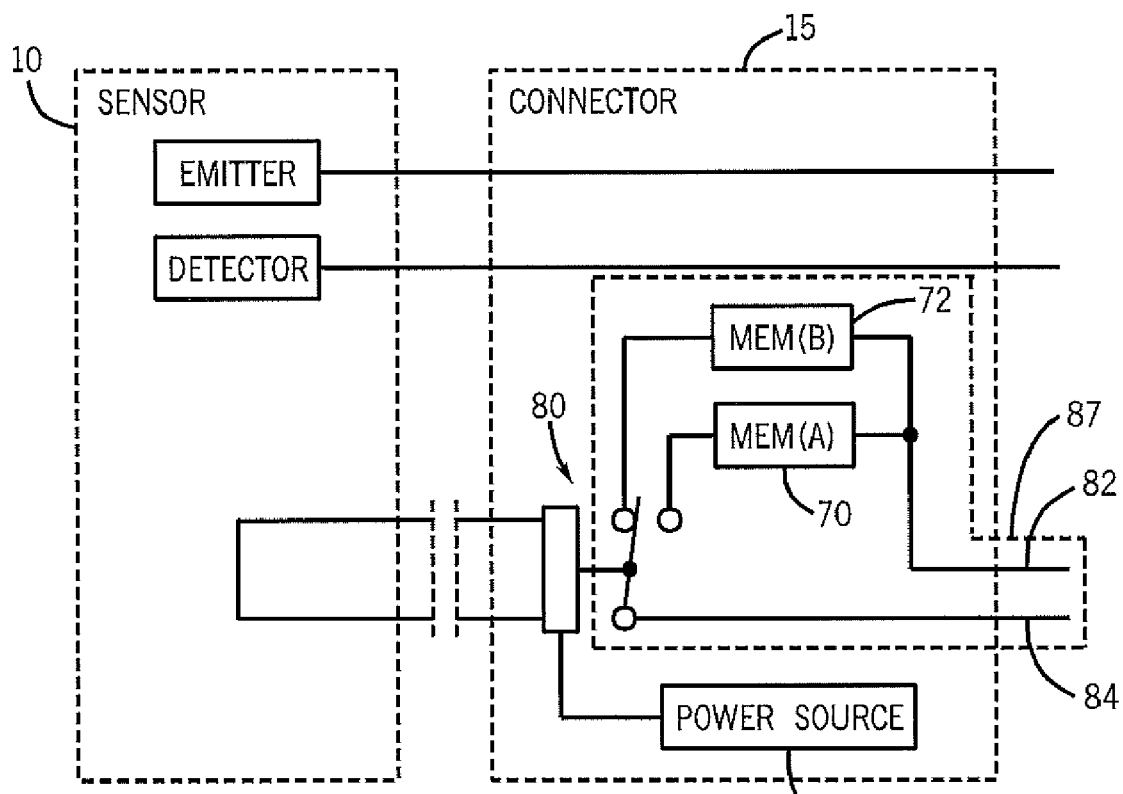

FIGS. 5A and 5B depicts the sensor connector 15 having a single pole double throw (SPDT) switch 80 that switches between the two memory devices 70 and 72. The first memory device 70 may store a first set (A) of calibration data (e.g., coefficients for algorithms stored on the monitor 12) and the second memory device 72 may store a second set (B) of calibration data (e.g., coefficients for algorithms stored on the monitor 12). Both the memory devices 70 and 72 are coupled to a first connection 82 (e.g., a pin, lead, wire, etc.) and switchably coupled to a second connection 84 (e.g., a pin, lead, wire, etc.). These connections 82 and 84 may be coupled to the monitor 12 via sensor cable 14.

The switch 80 may be driven by the continuity trace 34 in the sensor 10. Alternatively, in other embodiments the switch 80 may be provided in the sensor 10. In some embodiments the switch 80 provided in the connector 15 may draw current from the monitor 12 or an internal power source 86, such as a battery or scavenging circuit.

The sensor 10 may be applied to a first placement site corresponding to the first sensor configuration having an intact continuity trace 34 and electrical continuity in the trace 34. In this configuration, the switch 80 may connect the connection 84 of the connector to the memory device 70 storing the set A of calibration data. A readable circuit 85 is formed that includes the first memory device 70. Thus, in this sensor configuration having an intact conductive trace 34, the monitor 12 may read the set A (corresponding to a first sensor configuration and placement site) from the first memory device 70 via the readable circuit 85.

As described above and as shown in FIG. 5B, the sensor 10 may be modified for a second placement site by breaking the conductive trace 34 and modifying the sensor 10 to a second configuration. After modification of the sensor 10, there is electrical discontinuity in the conductive trace 34. The breaking of the conductive trace 34 may drive the switch 80 to connect the second memory device 72 to the connection 84 of the sensor connector. A readable circuit 87 is formed that includes the second memory device 72, and the first memory device 70 is now disconnected (and not included in any readable circuit). In this sensor configuration, the monitor 12 may then read the set B (corresponding to the second sensor configuration and placement site) from the second digital memory 72 via readable circuit 87. In some embodiments, as discussed above, the conductive trace breakage may be irreversible or reversible. If the breakage is reversible, reconfiguring the sensor 10 for use in the first sensor configuration by restoring electrical continuity of the conductive trace 34 may drive the switch 80 to connect the first memory device 70 to the connection 84 of the sensor connector 15, reestablishing the first readable circuit 85 that includes the memory device 70.

Figure 6A:
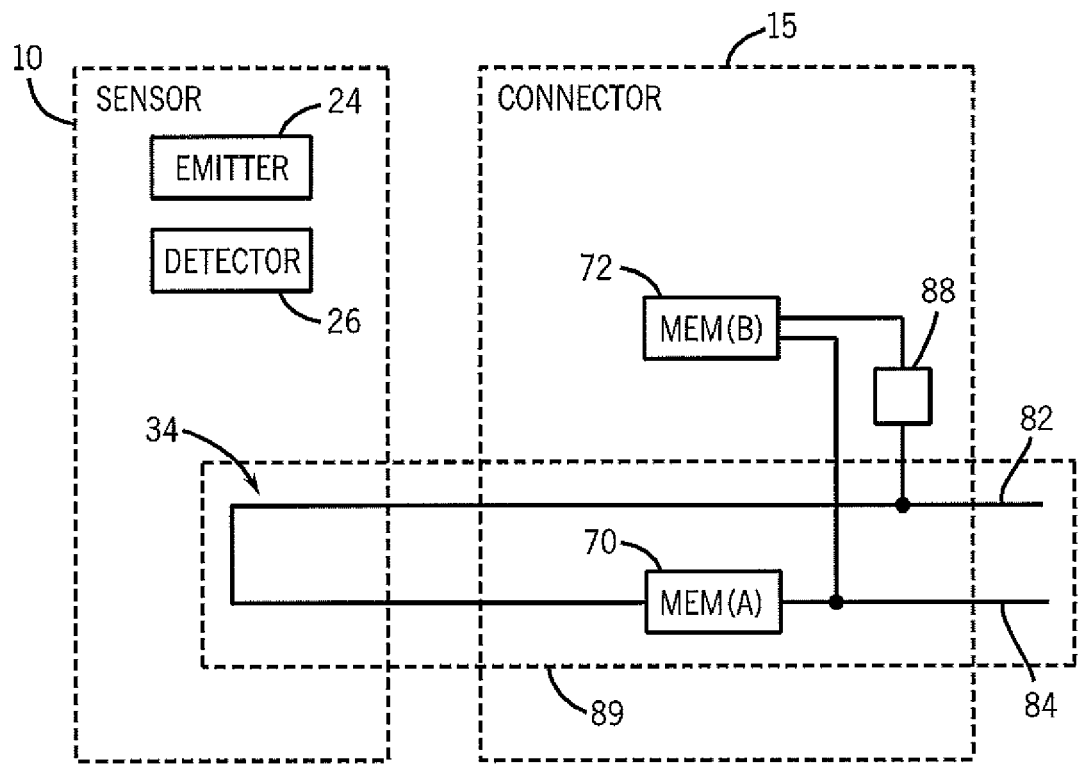
FIGS. 6A and 6B are block diagrams of a sensor and sensor connector having switchable memory devices in parallel with a component in accordance with another embodiment memory of the present disclosure.
Figure 6B:
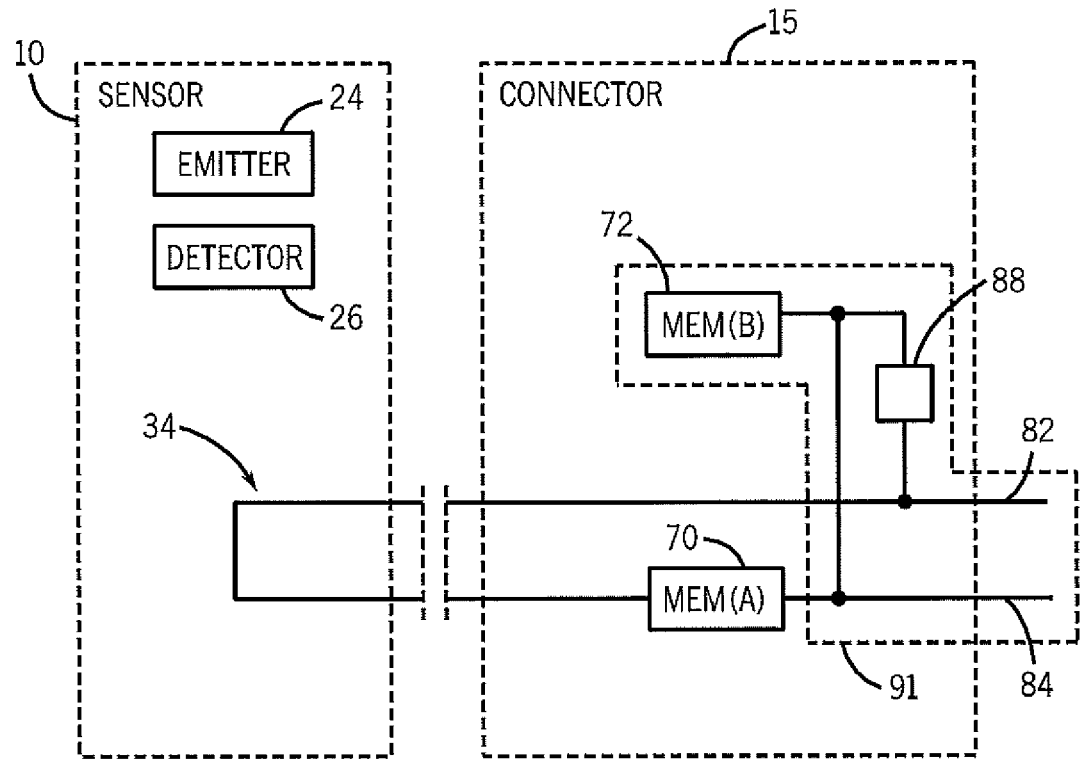

FIGS. 6A and 6B depict another embodiment of the sensor connector 15 in which the first memory device 70 and second memory device 72 are connected in parallel through a component 88. As shown in FIG. 6A, both memory devices 70 and 72 are coupled to the connections 82 and 84. The first memory device 70 may store a first set (A) of calibration data (e.g., coefficients for algorithms stored on the monitor 12) and the second memory device 72 may store a second set (B) of calibration data (e.g., coefficients for algorithms stored on the monitor 12). The component 88 may be selected to prevent the second memory device 72 from being read by the monitor 12 in a first sensor configuration when the conductive trace 34 is intact. The component 88 may be any suitable inactive or active component, such as a resistor, inductor, capacitor, diode, or any combination thereof coupled in series with the second memory device 72.

In a first sensor configuration having an intact conductive trace 34 as described above, the monitor 12 may only read the first memory device 70. In this sensor configuration, a readable circuit 89 is formed that includes the conductive trace 34 and the memory device 70. The component 88 may block the second memory device 72 from being read by the monitor 12, as the readable circuit 89 having the conductive trace 34 and first memory device 12 has a lower impedance than component 88. Thus, in this sensor configuration having an intact conductive trace 34, the monitor 12 may read the set A (corresponding to a first sensor configuration and placement site) from the first memory 70 via readable circuit 89.

As shown in FIG. 6B and as described above, the sensor 10 may be modified for a second placement site by breaking the conductive trace 34 and modifying the sensor to a second configuration. In the second configuration, the lack of electrical continuity in the broken conductive trace 34 blocks the monitor 12 from reading the first digital memory 70. The breaking of the conductive trace 34 enables formation of a readable circuit 91 that includes the second memory device 72 and the component 88. In this sensor configuration, the monitor 12 may read the set B (corresponding to the second sensor configuration and placement site) from the second digital memory 72 via readable circuit 91. In some embodiments, as discussed above, the conductive trace breakage may be reversible. In such an embodiment) restoring electrical continuity of the conductive trace 34 may reestablish the readable circuit having the first memory device 70, enabling the monitor to only read set A from the first memory device 70.

Figure 7A:
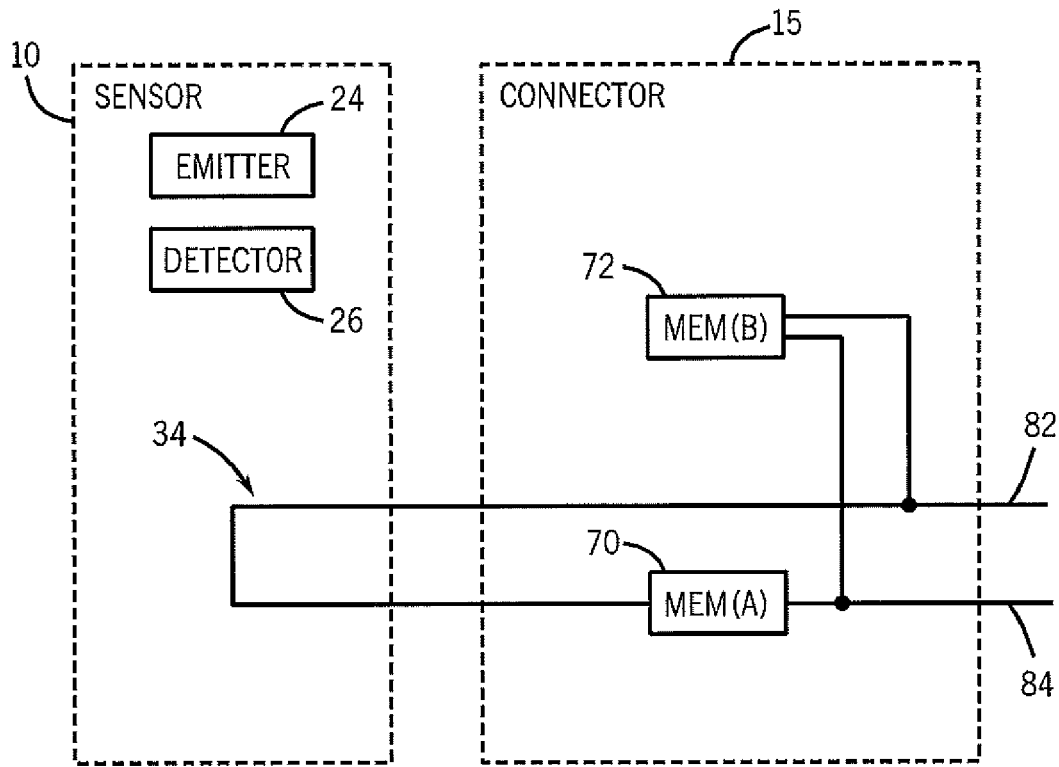
FIGS. 7A and 7B are block diagrams of a sensor and sensor connector having switchable memory devices in parallel in accordance with another embodiment memory of the present disclosure.
Figure 7B:
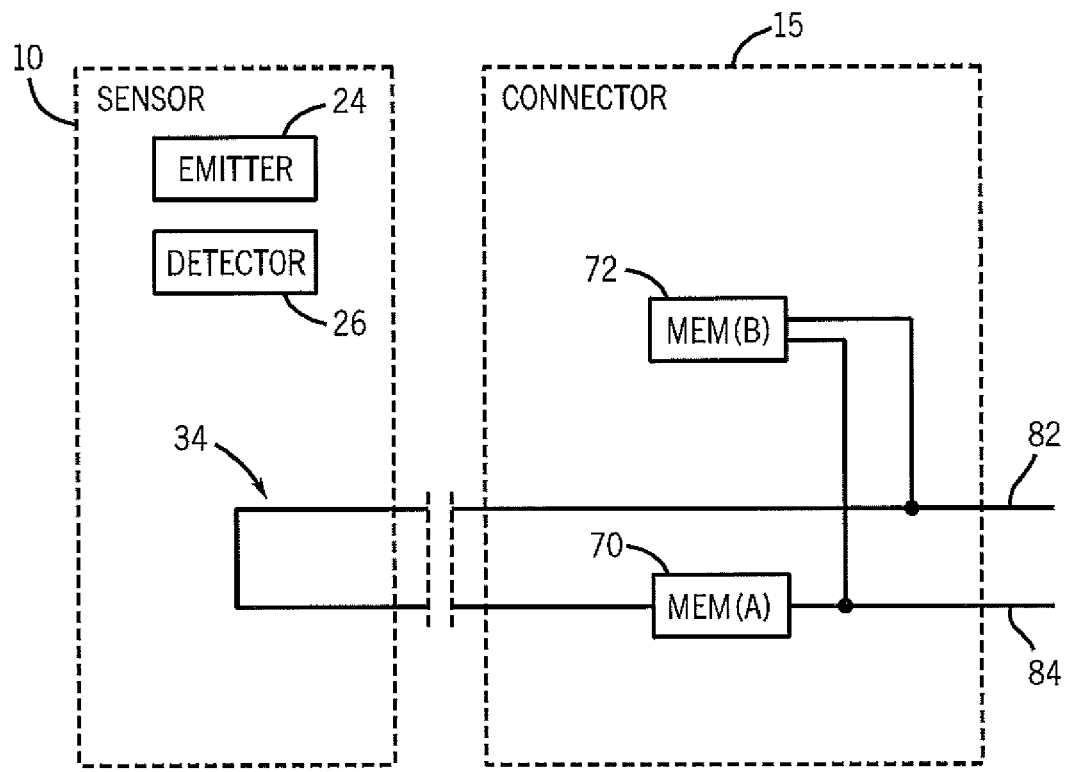

FIGS. 7A and 7B depict another embodiment of the sensor connector having the first digital memory 70 and second digital memory 72 coupled in parallel. In the embodiment, both memory devices are directly coupled to the outputs of the sensor connector 82 and 84 without any intermediate components. Again, the first memory device 70 may store a first set (A) of calibration data (e.g., coefficients for algorithms stored on the monitor 12) and the second memory device 72 may store a second set (B) of calibration data (e.g., coefficients for algorithms stored on the monitor 12). In the embodiment depicted in FIGS. 7A and 7B, the monitor 12 may be configured to only read the first memory device 70 if both memory devices 70 and 72 are detected.

In the first sensor configuration, as shown in FIG. 7A and as described above, the conductive trace 34 is intact and the sensor 10 may be placed on a first sensor placement site. In this configuration, the monitor 12 may detect both memory devices 70 and 72. The monitor 12 may be configured, such as by reprogramming the detector/decoder 67 and/or providing a software update to the monitor 12, to only read calibration data from the first memory device 70. In addition, this functionality may include additional information stored in the first memory device 70 that indicates the data stored in the first memory device 70 should be used by the monitor 12 instead of any other data or memory device available to the monitor 12. Thus, for the first sensor configuration depicted in FIG. 7A, the monitor 12 reads the set A of calibration data corresponding to the first sensor placement site.

As shown in FIG. 7B, the sensor 10 may be reconfigured for the second sensor placement site by breaking the conductive trace 34, as described above. After the conductive trace 34 is broken, the first memory device 70 is no longer in a readable circuit and is inaccessible by the monitor 12. The second memory device 72 is in a readable circuit coupled to connections 82 and 84. In the second sensor configuration, the monitor 12 may only read the second memory device 72 and reads set B of calibration data corresponding to the second sensor placement site. Again, in some embodiments, the conductive trace break may be reversible. In such an embodiment, restoring electrical continuity of the conductive trace 34 may reestablish the readable circuit having both memory device 70 and 72, enabling the monitor to read set A from the first memory device 70 as described above.

Figure 8A:
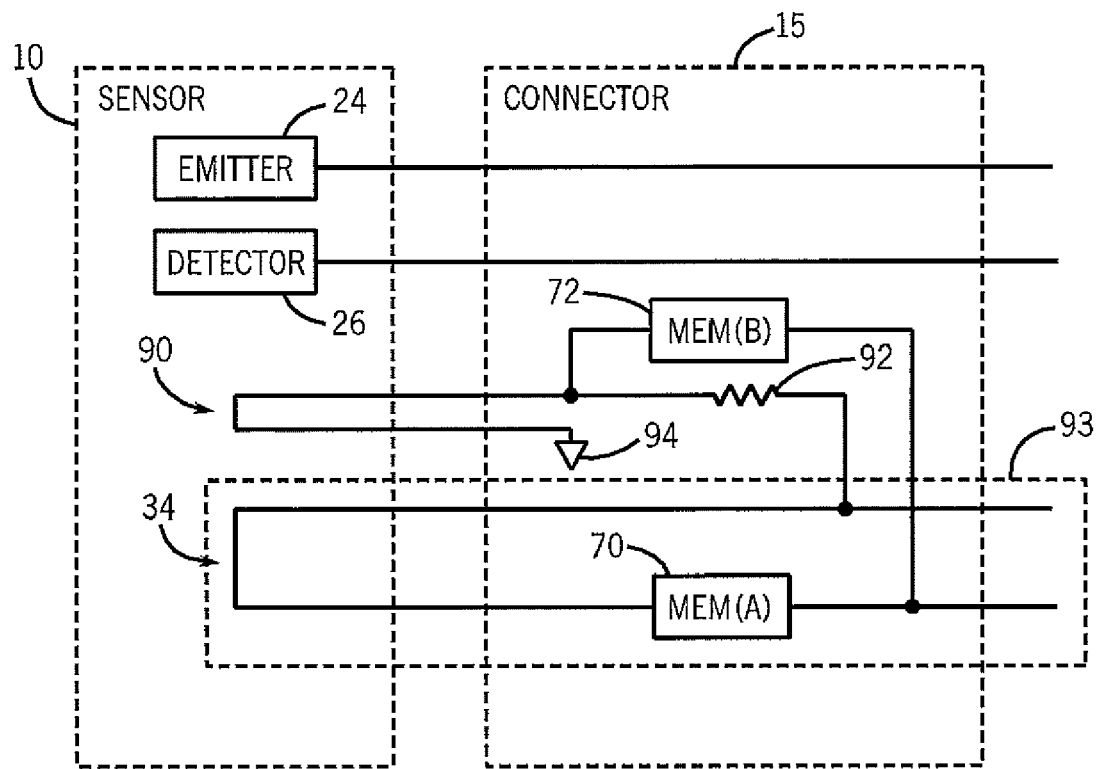
FIGS. 8A and 8B are block diagrams of a sensor having dual conductive traces and a sensor connector having switchable memory devices in parallel in accordance with another embodiment memory of the present disclosure.
Figure 8B:
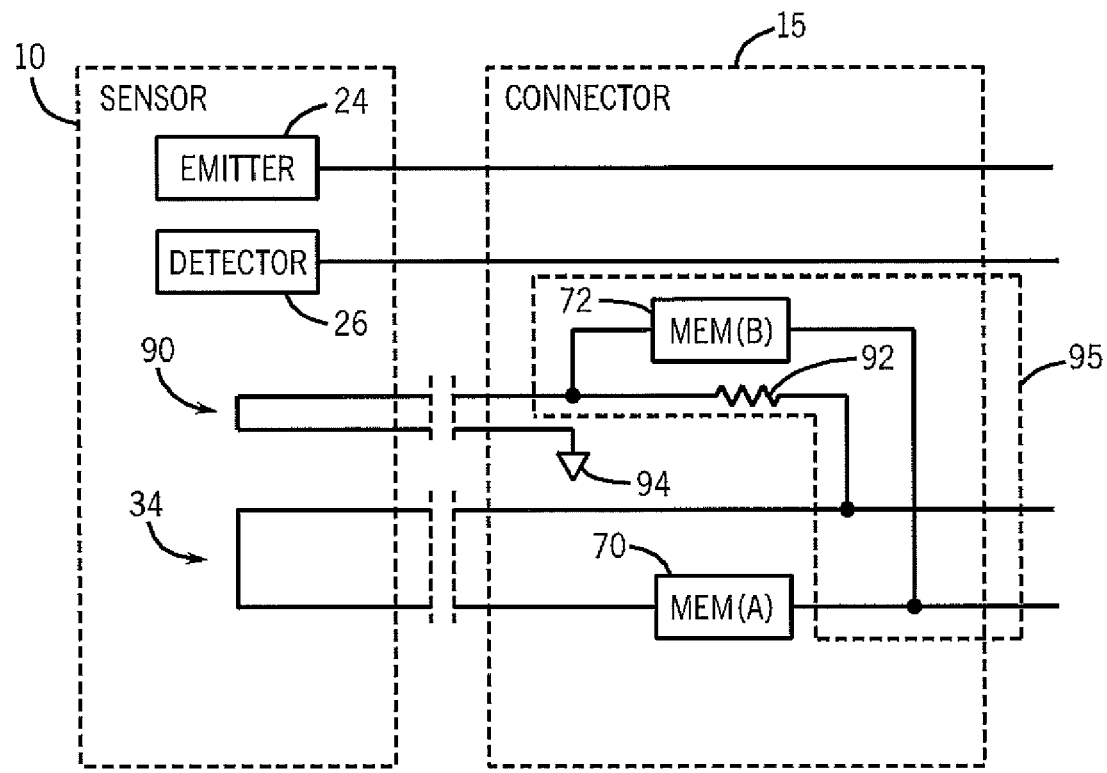

FIGS. 8A and 8B depict yet another embodiment of the sensor connector 15 coupled to a sensor 10 having a first conductive trace 34 and second conductive trace 90 (referred to as "dual tear-away traces"). The second conductive trace 90 may be configured similar to the first conductive trace 34 described above, such as by extending through the detecting portion 28 and into the removable portion 30 of the sensor 10. Again, the first memory device 70 may store a first set (A) of calibration data (e.g., coefficients for algorithms stored on the monitor 12) and the second memory device 72 may store a second set (B) of calibration data (e.g., coefficients for algorithms stored on the monitor 12). Each memory device may be coupled to the connections 82 and 84 for connection to the monitor 12. One or more resistors 92 may be coupled between the second memory device 72 and the connection 82, and one end of the second conductive trace 90 may be coupled to a ground connection 94. The electrical continuity of both the first conductive trace 34 and the second conductive trace 90 may be used to selectively switch readability of the memory devices 70 and 72 by the monitor 12.

In a first sensor configuration, the first conductive trace 34 and second conductive trace 90 are intact. As described above, the sensor 10 may be applied to a first placement site suitable for the first configuration. In this first configuration, the second memory device 72 is shorted to the ground connection 94 via the second conductive trace 90 and is not included in any readable circuit. Thus, in this configuration, the monitor 12 is unable to read the second memory device 72. The first memory device 70 is in a readable circuit 93 formed by the second conductive trace 34 and is the only memory device readable by the monitor 12. Thus, in the first sensor configuration, the monitor 12 reads the set A of calibration data corresponding to the first sensor placement site. The resistor 92 may be selected to avoid pull-down of the signal from the first memory device 70 to the ground connection 94.

When the sensor 10 is reconfigured to a second sensor configuration, as shown in FIG. 8B, both the first conductive trace 34 and the second conductive trace 90 are broken (e.g., by separating the removable portion 30 of the sensor 10 from the detecting portion 28 of the sensor 10). After the second conductive trace 90 is broken, the second memory device 72 is disconnected from the ground connection 94. In this configuration, the second memory device 72 is in a readable circuit 95 accessible by the monitor 12, enabling the second memory device to be read by the monitor 12 via readable circuit 95. The first memory device 70 is no longer readable by the monitor 12, as the broken first conductive trace 34 removes the first memory device 70 from any readable circuit.

In the embodiments discussed above in FIGS. 5-8, the sensor 10 may be unplugged from the monitor 12 during reconfiguration and then plugged back into the monitor 12 to ensure the monitor reads any newly readable memory device. In other embodiments, the monitor 12 may be capable of accessing the newly readable memory device immediately after reconfiguration of the sensor 12 (i.e., without unplugging the sensor 12).

In some embodiments, the multiple configuration sensor 10 may include a memory device storing calibration data for multiple configurations and placement sites. As described above, in some embodiments, the monitor 12 may not be capable of monitoring the conductive trace or responding to modification of the sensor 10 for application to a different sensor site. Thus, even if the sensor 10 stores multiple sets of calibration data for multiple sensor configurations and placement sites, the monitor 12 may not be configured to select the appropriate calibration data for a specific configuration and placement site.

Figure 9:
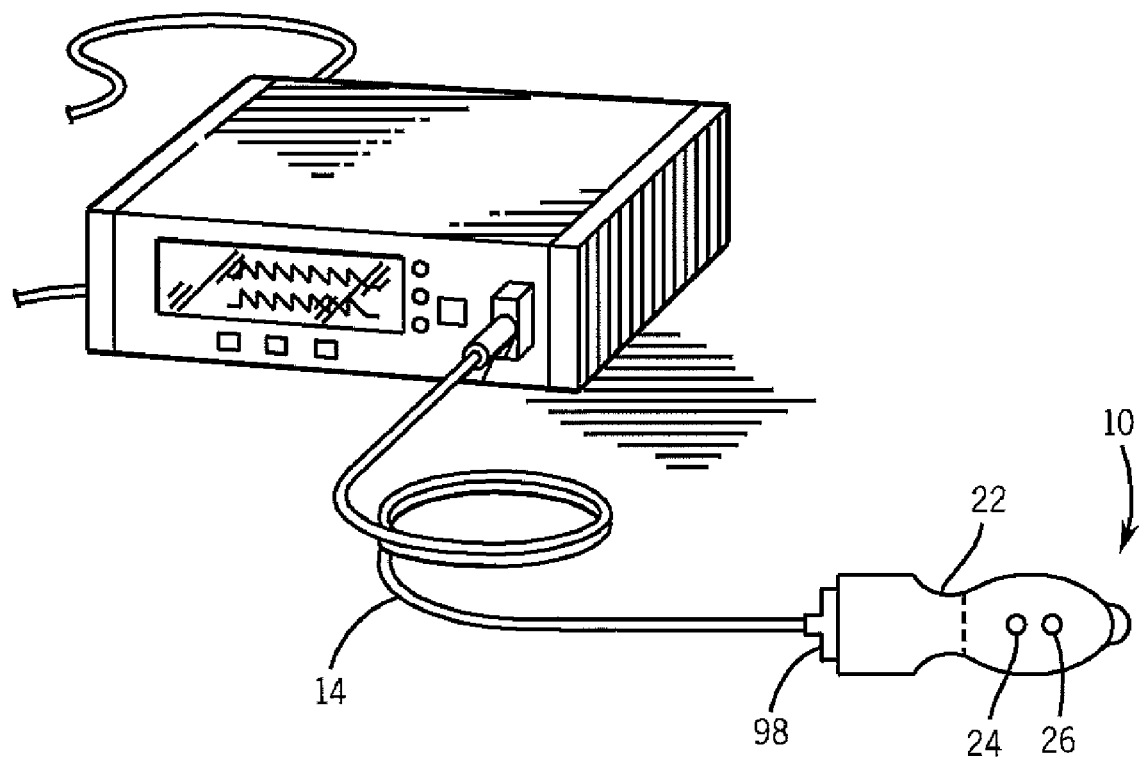
FIG. 9 illustrates a multi-parameter patient monitor, a sensor, and a sensor adaptor in accordance with an embodiment of the present disclosure.

In such an embodiment, an adaptor may be installed between the sensor 10 and monitor 12. FIG. 9 depicts a sensor adaptor 98 having a sensor memory processing circuit 100 installed between the sensor 10 and the monitor 12. As described below, the sensor adaptor 98 may interpret calibration data from the sensor 10 and provide the appropriate calibration data to the monitor 12 for the present sensor configuration and placement site. For all other information, e.g., data from the emitter 24 and detector 26, the sensor adaptor 98 may "pass through" the data to the monitor 12 without any processing. Thus, the monitor 12 receives the same data from the sensor but may receive different calibration coefficients from the sensor adaptor.

Figure 10A:
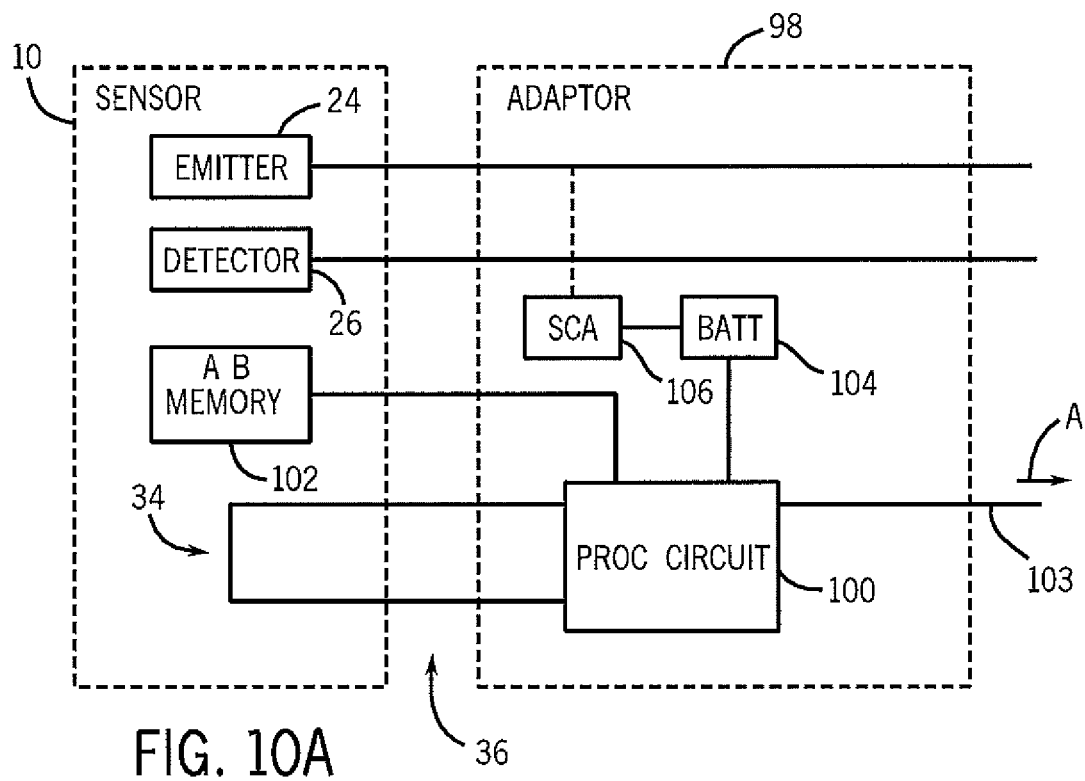
FIGS. 10A and 10B are block diagrams of the sensor and sensor adaptor of FIG. 9 in accordance with another embodiment memory of the present disclosure.
Figure 10B:
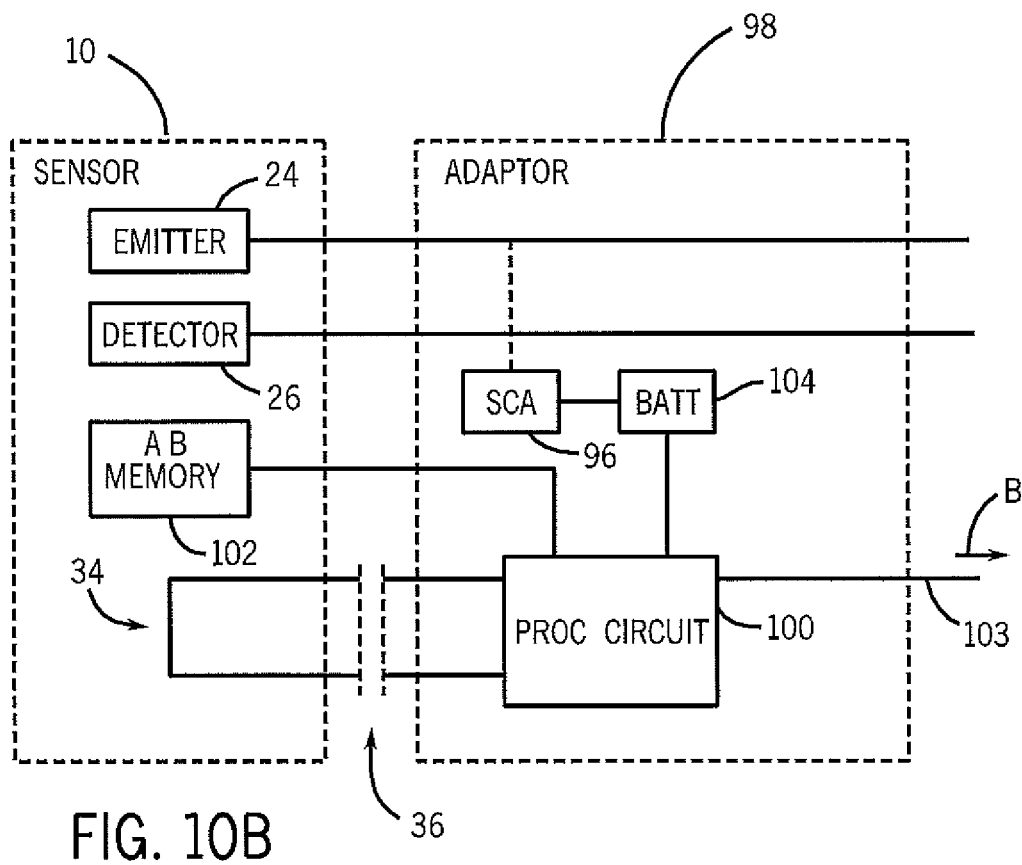

FIGS. 10A and 10B depict first and second configurations of the sensor 10 and the operation of the sensor adaptor 98 in accordance with an embodiment of the present disclosure. As described above, the sensor 10 may include a conductive trace 34 coupled to leads 36, such that the adaptor 98 may monitor the electrical conductivity of the conductive trace 34. Additionally, the sensor 10 includes a memory device 102 (e.g., a memory chip) that may store calibration data (e.g., calibration coefficients). It should be appreciated that the memory device 102 may be located on the detecting portion 28 of the sensor 10 so that the memory device 102 is accessible in any configuration of the sensor 10. The memory device 102 may store, for example, a first set (A) of calibration data for a first sensor configuration and a second set (B) of calibration data. The processing circuit 98 may read and/or intercept data from the memory 102 and output data to the monitor 12 over output 103 (e.g., one or more pins, leads, wires, etc.).

The adaptor 98 may include a power source, such as a battery 104, a scavenging circuit 106, or a combination thereof, to supply power to the processing circuit 100. The scavenging circuit 106 may scavenge power from the drive signal supplied to the emitter 26 (the drive signal for an LED) and may charge the battery 104 or a capacitor or other energy storage device to power the processing circuit 100. The battery 104 may provide direct power for the processing circuit 100 of the adaptor 98.

To enable calibration of the monitor, the processing circuit 100 may detect electrical continuity or discontinuity in the conductive trace 34, intercept the data from the memory 102, and select the appropriate calibration data. Any additional data received from the memory 102 may be passed through to the monitor 12 without any processing. For example, as shown in FIG. 9A and as described above, a first configuration of the sensor 10 may include an intact conductive trace 34 for application of the sensor 10 to a first placement site. The processing circuit 100 may recognize this configuration by the electrical continuity of the conductive trace 34. In this configuration, the processing circuit 100 may intercept or read any data from the memory 102 and select the calibration data for the first configuration. For example, the processing circuit 100 may provide the set A of calibration data to the monitor 12 via output 103.

As shown in FIG. 9B and as discussed above, a second sensor configuration may include a broken conductive trace 34, such as by separating the removable portion 30 from the detecting portion 28 for application to a second placement site. In this configuration, the processing circuit 100 may detect an electrical discontinuity in the conductive trace 34 to recognize the second configuration of the sensor 10. The processing circuit 100 may intercept or read data from the memory 102 and select the calibration data for the second configuration. For example, the processing circuit 100 may provide the set B of calibration data to the monitor 12 via output 103.

In some embodiments, the calibration data stored in the memory 102 may be encrypted. In such an embodiment, the processing circuit 100 may decrypt data from the memory 102, select the appropriate calibration data (based on the electrical continuity or discontinuity of the conductive trace 34) and re-encrypt the data. The processing circuit 100 may provide the re-encrypted data to the monitor 12 via output 103. The monitor 12 may process the data as if received directly from the memory 102 of the sensor 10. Thus, the monitor 12 does not perceive the sensor adaptor, but processes the "pass-through" data and the re-encrypted data as if received directly from the sensor 10.

In some embodiments, the adaptor 98 may be a separate component having male and female connectors for placement between the sensor 10 and the sensor cable 14. Alternatively, in some embodiments the sensor cable 14 may provide an electronic connection to the conductive trace 34 and the adaptor 98 may include male and female connectors for placement between the sensor cable 98 and the monitor 12.

In yet other embodiments, the sensor adapter 98 may be integrated into the sensor cable 14, such as by incorporation at the distal (sensor) end of the sensor cable 14 or at the proximal (monitor) end of the sensor cable 14. In such an embodiment, if the adaptor 98 is incorporated at the proximal (monitor) end of the cable, the adaptor 98 may use power directly from the monitor 12 if provided at the connection to the monitor 12.

What is claimed is:

1. A system, comprising:
a monitor;
a sensor configured to be coupled to the monitor, the sensor comprising:
a sensor body being configurable between a first configuration adapted to be applied to a first tissue site and a second configuration adapted to be applied to a second tissue site, wherein the sensor is configured to measure a physiological characteristic and wherein the second configuration results from separating a removable portion from the sensor body; and
a component coupled to the sensor, comprising:
a first memory device storing a first set of calibration data;
a second memory device storing a second set of calibration data;
wherein only the first memory device is accessible by the monitor in the first configuration and only the second memory device is accessible by the monitor in the second configuration.

2. The system of claim 1, wherein the monitor comprises a pulse oximetry monitor.

3. The system of claim 1, wherein the component comprises a sensor connector or a sensor cable.

4. The system of claim 1, wherein the sensor comprises an indicator circuit configured to indicate the first configuration or the second configuration.

5. The system of claim 4, wherein the indicator circuit comprises a conductive trace, wherein the conductive trace is intact in the first configuration and broken in the second configuration.

6. The system of claim 4, wherein the component comprises a switch configured to switch between the first memory device and the second memory device based on the indicator circuit.

7. The system of claim 4, wherein the component comprises a resistor, capacitor, inductor, diode, or other electronic component or combination thereof configured to block access to the second memory device in the first configuration and to permit access to the second memory device in the second configuration.

8. The system of claim 4, wherein the second memory device is connected to a ground connection in the first configuration and the second memory device is isolated from the ground connection in the second configuration.

9. The system of claim 1, wherein the component comprises a processing circuit configured to provide the first set of calibration data to the monitor in the first configuration and provide the second set of calibration data to the monitor in the second configuration.

10. A medical sensor, comprising:
a sensor body;
a circuit operably coupled to the sensor body comprising:
a first memory device; and
a second memory device, wherein the circuit is configured to make the first memory device electrically accessible only when the sensor body is in a first configuration and configured to make the second memory device electrically accessible only when the sensor body is in a second configuration, wherein the second configuration results from separating a removable portion from the sensor body.

11. The medical sensor of claim 10, wherein the circuit comprises a switch configured to make the first memory device accessible only in the first configuration and configured to make the second memory device accessible only in the second configuration.

12. The medical sensor of claim 11, wherein the switch is configured to make either the first memory device or the second memory device accessible, based on electrical continuity of a conductive trace of the medical sensor.

13. The medical sensor of claim 10, wherein the first memory device and second memory device are connected to the circuit in alternative series.

14. The medical sensor of claim 10, wherein the circuit comprises a resistor, inductor, capacitor, diode, or combination thereof configured to block the second memory device from being electrically accessible when the medical sensor is in the first configuration.

15. The medical sensor of claim 10, wherein the circuit comprises a continuous conductive trace configured to make only the first memory device accessible when the medical sensor is in the first configuration.

16. The medical sensor of claim 10, wherein the circuit comprises a broken conductive trace configured to make only the second memory device accessible when the medical sensor is in the second configuration.

17. A system, comprising:
a sensor, comprising:
a sensor body having a first configuration adapted to be applied to a first tissue site and a second configuration adapted to be applied to a second tissue site, wherein the sensor is configured to measure a physiological parameter;
a first conductive trace disposed within the sensor body, wherein the conductive trace is intact in the first configuration and the conductive trace is broken in the second configuration;
a second conductive trace disposed within the sensor body, wherein the second conductive trace is intact in the first configuration and the second conductive trace is broken in the second configuration; and
a component coupled to the sensor, comprising:
a first memory device coupled to the first conductive trace; and
a second memory device coupled to the second conductive trace, wherein only the first memory device is electrically accessible in the first configuration of the sensor and only the second memory device is electrically accessible in the second configuration of the sensor.

18. The system of claim 17, wherein the second memory device is coupled to a resistor and an internal ground connection of the sensor when the second conductive trace is intact.

19. The system of claim 18, wherein the second memory device is disconnected from the ground connection when the second conductive trace is broken.

20. The system of claim 17, wherein the first conductive trace and first memory device form a readable circuit in the first configuration.

* * * * *